United States Patent [19]
DasSarma et al.

[11] Patent Number: 6,008,051
[45] Date of Patent: Dec. 28, 1999

[54] RECOMBINANT VECTOR AND PROCESS FOR CELL FLOTATION

[75] Inventors: Shiladitya DasSarma, Amherst, Mass.; John Halladay, Madison, Wis.; Wai-lap Ng, Amherst, Mass.

[73] Assignee: University of Massachusetts, Amherst, Mass.

[21] Appl. No.: 08/680,897

[22] Filed: Jul. 16, 1996

Related U.S. Application Data

[63] Continuation of application No. 08/271,270, Jul. 6, 1994, abandoned, which is a continuation of application No. 07/944,581, Sep. 14, 1992, abandoned.

[51] Int. Cl.$^6$ ............................. C12N 1/21; C12N 15/70; C12N 15/11
[52] U.S. Cl. ................. 435/476; 435/252.33; 435/320.1; 536/23.1; 536/23.7
[58] Field of Search ................................ 435/69.1, 172.1, 435/172.3, 320.1, 325, 252.3, 252.33, 254.1, 254.11, 254.2; 536/23.1, 23.7

[56] References Cited

PUBLICATIONS

Blaseio et al. "Transformation of *Halobacterium halobium*: Development of Vectors and Investigation of Gas Vesicle Synthesis" PNAS, vol. 87, pp. 6772, 6776, Sep. 1990.

Jones et al. "Structure and Organization of the Gas Vesicle Gene Cluster on the *Halobacterium halobium* plasmid PNRC 100." Gene, vol. 102 (1991) pp. 117–122.

DasSarma et al. (1987) "A Plasmid–Encoded Gas Vesicle Protein Gene in a *Halophilic Archaebacterium*" *Molecular Microbiology* 1, 3650370.

DasSarma et al. (1988) "High–Frequency Mutations in a Plasmid–Encoded Gas Vesicle Gene in *Halobacterium Halobium*", *Proc. Natl. Acad. Sci. USA* 85, 6861–6865.

Horne et al. (1988) "Two Genes Encoding Gas Vacuole Proteins in *Halobacterium Halobium*", *Mol. Gen. Genet.* 213, 459–464.

Horne et al. (1991) "A DNA Region of 9kbp Contains all Genes Necessary for Gas Synthesis in *Halophilic Archaebacteria*", *Molecular Microbiology* 5, 1159–1174.

Jones et al. (1989) "Analysis of Insertion Mutants Reveals Two New Genes in the pNRC100 Gas Vesicle Gene Cluster of *Halobacterium Halobium*", *Nucleic Acids Research* 17, 7785–7793.

*Primary Examiner*—David Guzo
*Attorney, Agent, or Firm*—Fish & Richardson, P.C.

[57] ABSTRACT

The present invention is directed to a recombinant vector capable of directing the synthesis of gas vesicles in a non-floating cells. Cells transformed by the vector of the invention are also provided. The present invention is further directed to a method for conferring buoyancy to non-floating cells. The method of the instant invention is useful in harvesting cells, for example in fermentation processes, and in bioremediation, for example in conferring buoyancy to hydrocarbon-degrading bacteria.

9 Claims, 14 Drawing Sheets

ISH8
1   GTGAGTCTTAACTGAAGACGAATGCCGTGTCGGGATTGAGCGAGCAGAAA  50

51  CGCACCTCACGGACTCCGAAGTCCAGGAGAAGACCTCCTATGACGGGAAC  100

101 GTGGATCAGATCGAGACCTGCATCGTTTACGATGGAATCGACGAGGAATA  150

151 CCTCGAGAAGTGCCGGAACGAATGGGACAACTGCCGGGAAAAGCTAGAGA  200

201 AACTCGAAGAACAAACCGCCATCCTCACACAGGGACATGGAGAGTCATTG  250

251 CGGTTGCTCACTGGAGAGTTCGACTCTACTCGACTACAATCCCGCTTCGA  300

301 GAGCGGTATCGATCTCCCGGTGAATCCGAAGACAGAGTTCGTCGCTGCCG  350

351 TCCCCGGCAGTGGGCTCGTCGTTTGTCGCCGAACCCGATCCGGAACGACT  400

401 CCGATCAGCGAGAACAGTGGTCTTGCCCGTCCTGTCACCGAAAATTTCGC  450

451 TCACACCGCGGGTTACAGCGCCACTACGACACCAACCGCGAACACGCGGA  500

501 GGCGATGATCGACGTCGATCGGGAACTGGAGCAGGATGAGAGTACCAGCG  550

551 CCGGAACTGAATGGGTCGAGTTCGTCGACCGAGTTGAGACGTTCTGTAAA  600

601 CTCTCGGATGGATTCGACGAGAGTGAGATCACCGTCACGCACGATTCAGC  650

651 TACCCACTGCGTCCGTATCTCCGGCGCACACGAGAATTCAATCGATACGA  700

701 GTCCCGTCTCCGAGACGATCGACGGCGACGTGGAGTGGCGTTCGTCTGGA  750

751 CGCTACCTTGTCCTCTCGTTCCCGCTGTGAACCGGTGGTCTTTCGCCTCG  800

801 CCACCGCTGTGATTCAACATATCCCAGTTGGGTTTCCGCATTATCCCTCT  850

851 CCTTTATTCTCACGCGACACGACCTCGAATCAGTCCTCTCGCCGATCGGC  900
         gvpM***

901 AGTGGGCGAGGTCGTGAACGCTTCGCTCTGTTGTCGATGCGCAGCATCCC  950

951 ACTCCTCGAACAGGCCGTACTCCGTCATGGTGGTCATGCCAGCAATCGCT  1000

FIG. 6A

```
1001 GCCCGGAGGCTGATCCCGATCAGGGGAATGTCGGCGACCGTCACGATCAC 1050

1051 GTCCGCTTGAATCACGGCTCCGTCGCGCAGTAACACGTCGACGAACTCAA 1100
                      . <<<gvpM .
1101 CGATCGCGTGTGTCTCGTCTTTTGTTGGCTCCATTATTTACCAATATCTG 1150
                         gvpL***

1151 GCGCGAACGTGTACGGTGGCCACGGCCCCGTGAATCTGATCTCTACACCC 1200

1201 TCGTGTTCGACGATCGTATCCAATCGATCACCGAGAGCGGTCTCGTCGTC 1250

1251 CTCGTCCGCGAGAACGGCGAACCGCACGATCTGTTCTTTCTCGATGGACG 1300

1301 AGTGTTCGTCCTGTAGCGGCGTATTCGTGTCCTGTTCGGTCAGGTCGTTC 1350

1351 ACGACCGGGGTAATGGCCTCTTTCAGTTGATCTGCTAGTTCCGTCCGGCG 1400

1401 CTCTCGTTTCAGCTCTTGGAGTCGCTGATCGGACTGTTTCTCGAGGAGGA 1450

1451 ACTTTTTCCCTGCGCCCGATTGTTGCTGGCGCTGTCGTAGTTCTCGGAGC 1500

1501 CGGTCGTCTCGGTCTGCGATGGTCTCCTCGAACGGTGCGGAATCCCACAA 1550

1551 CAGATTGATTCGATACTCCCACACTCCCGCGAACGACGCTAATTCGTCGC 1600

1601 GGAAGCCCTCGTAGTGGTCTTCTAACCACCGTTCGATACTCGCATCACCG 1650

1651 CCCTCGAGGACCGTGTCGAATCGCATCGGCAGCGGCGTACCGAACGCGTC 1700

1701 GCTCGCCGCGTCGACGACCTGCTGGTGCGTGACCAGCCATCGCTTCACCT 1750

1751 GTTCGAGGTCTTCCGTCTCGTAGACCGTCTCACAGTCATGGACGACGGCG 1800

1801 CCCACGCCATCGGCCTCGACGACGTAGACAGGGTTGTCGTCGACCCCGGT 1850

1851 CGTGGACAGGGTCGCCGATTCCGACGACGTGGTATCGACCACGCAGTATA 1900

1901 GATAGCGGCCGTTGCTGACCGTCCGTTCCTCGTTCGCTGTGGTCTGCTCT 1950
                      <<<gvpL
1951 TCTTCCGGGCTGGGCCGGTGGTCAGTCATACGTCATCACGCTGGGATTCC 2000
                         gvpK***

2001 GGCGAGCCGTGACCTGACGGTGTCTCGTGCTCGGATAGCTGTTCGATGGC 2050
```

FIG. 6B

```
2051 GTCGCGGATCACGTGATCGAGGTCCTCCCTAAACTCGGAGACCTCGGCGT 2100

2101 TGATATCCTCTTGCTGTTTCAGTCGCTCGAGCTCGTCTTCGAGGGCCTGT 2150

2151 AATTGTCGCCCCAATCGTTCGATTTCGTCCTCTGAGAGCGACCCGGATTC 2200

2201 CATCCGACGCACCGCTTCTTGTTCGAGGGCCTCGACCAGCAATTCGACGA 2250

2251 CAGTTACGACCAGCGCCGTGAGCCCGCCTTGCAAATCGTCCGCGTCGTCG 2300
              <<<gvpK
2301 TCGAGTGCTAGTTCCATCTCATTTGGTCTCCTCCGCTGACGTGGATGCCG 2350
        gvpJ***

2351 TCGGCGTCGAATCGTCCGACAGTGGGTTCGTCGACTCGGTCTCCGATTGG 2400

2401 GTTTCCGACGCCGGGTCGGACTGGTCCGGTGAGATATTCGCGGCGGACTC 2450

2451 GACGCGCTCCATATCCGTCCCCGTTGGGAACTCGAGCCCGTATTCGGCCG 2500

2501 CTGTCTCGAACGAAGCAATCGCGGCCCGTAACTCGATACCGAGGAGTTCC 2550

2551 GTGTCCCCGACGCTGACTGCGATATCCGCGTTGACGACGACTCCTTTGTC 2600

2601 TAGGAGCATCTCCAGCATCTCGGCGAGGTCGCCCTGCGAGCGCGTCGGTT 2650
         .<<<gvpJ
2651 TGGGGTCACTCATCGTTCACCTCGTCCTCAGTGGGACTCCCGGACGCGCT 2700
        gvpI***

2701 CTCATCCGACGGGGCGGATGCCTCCGAGTTTCCACCGGCTGTTTTCTGGT 2750

2751 GAAGCCGTTGGCCGTACAATCGCTCTCGAGCCGTCACATCCGAGTACTTC 2800

2801 GGAGTCTTCGGGACGGTCGAGTGGGAGTTGCGTACCGCGTTCTCCGCGTT 2850

2851 CGACTTCTGAGGCGGCATCGTCGAGTGAGCCGCTGGATTCTTGACCGTCT 2900

2901 CCCCGTCAGTATCGTCGCCGTCGGAATCGTCACGCCGGGGTTCCGACTGT 2950

2951 TTCCGGTTGCGGGTCCGACGCCGGGCGAGTTTTTCGCGCTGCCGAAGCAG 3000

3001 ATTGCGCCGGGCTTTATCGCGGTTGATCTGCGCCTTTACTCGTGCCTGTC 3050
```

FIG. 6C

```
              <<<gvpI
3051  GTGCTTTCTGCTTGTGTTTTTGCTGTTGTTTGTCGCTCATGTGGATTCAC  3100
                gvpH***

3101  CTCCATCGGTGTCCGATGTTCGTGCTAGCCGAATTTCGAGAACCTGATTT  3150

3151  CTGAGAGTCATATCGGTGATCGCCACGTCCGGCCGGTCGAGTACGACTCG  3200

3201  CTCGACCACGTCGTCGTCGACGCGTAGCGTGAGTGCCTGCTCGTCGGTAT  3250

3251  CGAGTGCGACGTCGACGTCGTCGTCCGTCACGCCCGGCAAATCTGCGACC  3300

3301  ACGACGAGTTCGTCGCCGCTCGTTCCTCCACGAGTCTCGACGTGAATCGA  3350

3351  ATCCTCCGTCGTCCTTTGCTGACCGGATCGCTGTTCGGAGCGGGACCGAT  3400

3401  TGGACGATGGTTCCTCGTCGTAGGACGACCCGTCCGCTCGTCCCAGCCCG  3450

3451  ATGGAAACGTCGTAGTCGTAATCAATTCGGGCGTTTCCCCGGTCGATACG  3500

3501  GCCTGACTCGTGTCGGTGACCGCCCTCCTCTTCGATGTCGGCGAGCACCT  3550

3551  CGACGAGCGTGTGCAATTGGTCGAGCAGCCCGCTGAGCTGGGAAGACTGG  3600
              <<<gvpH.
3601  TCGTCGGACGCGTCGTCGTTTTCGTCGGGTACCATTATTTCTTGACCTCC  3650
                gvpG***

3651  ATGCGGTCACGCATCTGTTCTTGGACCTGCTCGGCCATCTCCAGTTGCGA  3700

3701  TTCGAGTGCTTGCTTGCGCTGCTGGTACTCCTCGTCGGATCGTTCACCAA  3750

3751  CTTCGTACAGGAGTTGGTTCTCCTTGATGTCGTCTCGAATCGATTTGGTG  3800

3801  TCGTACATCTCGTCGAGAGCCATCGTCTGGAGGATATCCAGCAAGGAGAA  3850
              <<<gvpG
3851  AAACGGGCTCACGAAGAGATCGTCTATGATGAACATGCATTATCGGCCTC  3900
                gvpF***

3901  CTTGTTGCTGTTCCGCGCCGATGTGAATGTCCACGAAATTGTACGGCGGC  3950

3951  CACGGCCCCGTGTACTGAATCGTCAGTTCGTCGTATTCCGCTTCGACATC  4000

4001  GTCGATGGCGGAGTCGAAAGCATCGCGTTTCTCGAAGTCGACGAGGTACG  4050
```

FIG. 6D

```
4051 ACTTATTGATGATCAGGCGGTCTGTGAAGAGATCGTTCTCGGTCTCGTTG 4100

4101 ATACTCAGATCTGCTAGTTGATCCGTGACGTTTTCCTGGATTTCTTCTCG 4150

4151 AGGGACTGTATCGTCGCCAGGACCGAGTATCTTCACGCCAAGTTCGACGG 4200

4201 TTCCCTCGATGTCATTCAGCGTACTGCGCAATGCACGTCGCGCCCCGCGC 4250

4251 AATACACCCTTTAGCGTGCGCGCACTTTTGAACGCCATCCCGAAGCTCAT 4300

4301 CGGGACGACTGTGCGTTCTTCTTCGTGCTTCAATACCTCCTGGAGCACGT 4350

4351 TGTTATGAGCTTCCACGTCCTCATCGGTGCGCTCGGGGTCGGTCGTATCA 4400

4401 ATGTCAGAGACGACAGCGGAGAGTGTCTTGTAATCGACCGTATAGACCTG 4450

4451 TTCCGCTCCGGCAACGCCTTCGACATCTAATTCGAGATCTTCCTGTTCGA 4500
                        <<<gvpF
4501 TGATACCGTATGTGTATAGGTTCTCAGTCATTGGTCTCTCTTCCTTGGGA 4550
     gvpE***
4551 TTGTGATTGACGCGCCTTGCAATCGGTCATAACCGCCTTGAGTACGAGCG 4600

4601 AAAACAGCAGCAACTGATCAACCATGTGGTCTATTCGGGTGAACGCTCCT 4650

4651 TCAGGATCGGAGAGGCGATACACTTTGCGCTTGCTCAATTTCTGTACCTC 4700

4701 AAGTACACCTTCGACTGCAAGGTCATTTAAATGCGGGTATACTGTACCCG 4750

4751 GACTCAGGTCTGCCCCAAACAGCCGCCGGAGATCCTGGAGCAGTTCTTTT 4800

4801 CCACAGGCACCGTCTCGCACAGTAATCAGAAGAAGGAGAATCTCGTCGAT 4850

4851 ATGTTCGGTGACGATGGCATCACTGATCGTGTGAAGCTGGTCATTATCAA 4900

4901 GCCACCCGTCCATCGTAGCGACCGCGTCATCAGTCAGCGGCGTGTCCGTG 4950

4951 TAGCGTTGCGTTGCCCCCTCATCAGGCGGCTGGTCTGCGTGATCTGACGC 5000

5001 ACCGTCGGATTCGATCACTGATTCGAGATCTGTGACTGCGAACGAGATCG 5050
                        <<<gvpE
5051 CGGCGTTAGCATCGATGTCTGCGGTGAGTTCCTCCAGCAAGTCGTCCATT 5100
```

FIG. 6E

5101 GTTAGACCATCTCCGTGAGCGTGATTTTGGGGATCGACTCTGACTGGCTG 5150
     gvpD***

5151 ATGCCGATTCCGAGCAGGGGCGTCAACGGGTTTTCGCCATACAGGATGAT 5200

5201 GGCGTCACCGGACCGTTCCAGCCGGAAGTGCATATCGGCAACCCGATCCG 5250

5251 CTCGCGTGCGGAGTTCAGTACCTTGCTTGGTGATGAGCAGTGTCAGGTCG 5300

5301 TTGTGGAGAGCGACGTAATTTGCAAAGTCACCTAGCCGGGTCTCAAATGC 5350

5351 CTCCTGCGCCGTGTCCATGCTGATCACGTGCAACAACGGATCTTCACTTT 5400

5401 CTTCTCGCACCTGTTCAACGTAGGCCATGTATGGCTCGTACGCGAGTTGC 5450

5451 CCGCCCTCTATCGGTGACTCAAAGTCCTCATCAATCGGATGCGGCTGGTC 5500

5501 ACTCCCCGTAACTCCATCCGTCGAACGTGAGCCATCGTCCGCACCATCAG 5550

5551 TCTCATGCGTCGCCGTCGGTGCATCGTCCGGCGGCGTTGTCGTTGCCATC 5600

5601 TCAGAAAATGACTCAGTGCTGTCCGGTTGGTCGTACCGATCCGCACTGTC 5650

5651 AGAGGGGCCGGCGTATGTTTCGAAGACGTGGCAGTAGGTATCGAAGACCT 5700

5701 GTGAGGAGAGCACAGTATTGAGATCGTTGTGGAGTAAGCCAGGGCTGCCC 5750

5751 TCCCGGGGCGGGACAACCGCAACCCCCATCTCCTGAGAGAGGAAGTTGCG 5800

5801 AATCGTCGGGAGCGTCAACACGCTCCACGCGTCACGAGACAGATCGGGCC 5850

5851 CGAGGTCGAGATGAACGACGCTGCCGCGGTTGTAGCCACCCGAGAGGATA 5900

5901 CGGTCAAGATCACGGATGCCAGTCGAGAATTTCGCCTTCGAATTTGCCAG 5950

5951 GGGATCCCACGTGCCATTCCCGGTTCCTGTTTGGATGGTTAGTAATTCGA 6000

6001 CCGGCGTGATCACCTGGAACTGGCCGTCGGCAAGCGTAAAGGGCTGTAAG 6050

6051 CGGTTGCCGATTCGAACGCCCCGAAGCTTATCCAAGCGGAGATCCCGACG 6100

FIG. 6F

```
6101 CGTTCGGCCACGGTCATCCTCCTTAACCTGGAGGGTGACGACCCCATCGA 6150

6151 CGATGTATTCAAGCGATGAGGGCGCCGCTGTTTCTGTCACTAACATCAGA 6200

6201 CGAATGTTCTCTTCGCGGGCAAGAACGGCCAGTTGATTCGTCACAGTCTT 6250

6251 GATGTCAGGGGGGTCATCGTGGCGAACAGCCAAATACTCGTAGATGAGTT 6300

6301 CCCAGCTATCGAATGCGATTGTGAGTTGCGTGGTCGCGGCGTTGATCTCT 6350

6351 TGGATCCATTCGAGGAGCGAATCCAGATCGAGTTTCTCGAATGGCACGTC 6400

6401 TACGTCCAGTGGGAGTTCGAATGGGTCTTGGAAGAGGTCAAGAATCGCGG 6450

6451 TTGTGTCGAGTGAGGAGTGATCGGCGAAGTACATCTCGTGAACCGTCTCC 6500

6501 TGATCAACACGTGTGGACACGTAGAGGACATCACTGTCTCGGTCCAACAC 6550

6551 ATCGAGGCCGCGGATCGTGAACAAGGTCTTACCCGTGCCTGGTGCACCGT 6600

6601 TAATGAGGAGCGTTTCCCCGGCGTCACCCATGAAAAACTGGCTGAGCTCG 6650

6651 CGGGGGAATAACACGATTCCGGTGTAGTCTGTGGGCGGGTGAGCTAGATT 6700
          <<<gvpD
6701 GGGTGAACTCATTACTTCTCTCCAGTCGATGGCGGTAGAGCACTCCCGAC 6750
                    $P_D$
6751 TAGTAGGTGAGGCTTTCTTCGCTTCACGACTGTCTAAGAAGCTTTACACT 6800

6801 CTCCGTACTTAGAAGTACGACTCATTACAGGAGACATAACGACTGGTGAA 6850
                    $P_A$
6851 ACCATACACATCCTTATGTGATGCCCGAGTATAGTTAGAGATGGGTTAAT 6900
          gvpA>>>
6901 CCCAGATCACCAATGGCGCAACCAGATTCTTCAGGCTTGGCAGAAGTCCT 6950

6951 TGATCGTGTACTAGACAAAGGTGTCGTTGTGGACGTGTGGGCTCGTGTGT 7000

7001 CGCTTGTCGGCATCGAAATCCTGACCGTCGAGGCGCGGGTCGTCGCCGCC 7050

7051 TCGGTGGACACCTTCCTCCACTACGCAGAAGAAATCGCCAAGATCGAACA 7100
```

FIG. 6G

```
7101 AGCCGAACTTACCGCCGGCGCCGAGGCGGCACCCGAGGCCTGACGCACAG 7150
              ***gvpA
7151 GCCTCCCTTCGGCCGGCGTAAGGGAGGTGAATCGCTTGCAAACCATACTA 7200
                gvpC>>>
7201 TTAACACCTTCTCGGGTACACACTAATCCCATGAGTGTCACAGACAAACG 7250

7251 CGACGAGATGAGTACTGCCCGCGATAAGTTCGCAGAATCACAGCAGGAGT 7300

7301 TCGAATCATACGCTGACGAGTTTGCAGCCGATATCACGGCAAAGCAAGAC 7350

7351 GATGTCAGCGACCTTGTCGATGCGATCACCGACTTCCAGGCGGAGATGAC 7400

7401 CAACACGACGGATGCATTTCACACATATGGTGACGAGTTCGCCGCTGAGG 7450

7451 TTGACCACCTCCGTGCCGATATTGACGCCCAGCGGGACGTGATCCGTGAG 7500

7501 ATGCAGGATGCGTTCGAGGCATATGCTGACATCTTCGCTACAGATATCGC 7550

7551 AGACAAACAAGATATCGGCAATCTTCTGGCTGCGATTGAGGCGCTCCGAA 7600

7601 CAGAGATGAACTCAACCCACGGGGCATTCGAAGCATATGCGGACGACTTC 7650

7651 GCAGCCGATGTCGCTGCGCTCCGTGATATATCTGATCTGGTTGCAGCAAT 7700

7701 CGACGACTTCCAAGAGGAATTCATCGCCGTGCAGGACGCATTTGACAACT 7750

7751 ACGCTGGTGACTTCGATGCGGAGATCGACCAGCTCCACGCTGCCATCGCT 7800

7801 GACCAGCACGACAGCTTCGACGCTACCGCGGACGCCTTCGCAGAGTACCG 7850

7851 AGATGAGTTCTATCGCATAGAGGTGGAAGCACTGCTTGAGGCGATCAACG 7900

7901 ACTTCCAGCAGGACATCGGTGACTTCCGAGCGGAGTTTGAAACGACTGAG 7950

7951 GACGCGTTCGTTGCCTTCGCCCGTGACTTCTATGGCCACGAGATCACGGC 8000

8001 CGAGGAAGGCGCCGCCGAAGCGGAAGCCGAACCCGTCGAGGCTGACGCGG 8050

8051 ACGTCGAAGCGGAAGCAGAAGTCTCTCCAGACGAAGCTGGCGGAGAATCC 8100

8101 GCCGGTACCGAGGAAGAAGAGACAGAGCCGGCCGAGGTGGAAACAGCGGC 8150
```

FIG. 6H

```
8151 TCCAGAAGTAGAGGGGAGTCCTGCGGACACGGCAGACGAAGCGGAAGATA 8200

8201 CGGAAGCAGAGGAGGAGACAGAGGAAGAGGCACCGGAAGACATGGTGCAG 8250

8251 TGCCGGGTGTGCGGCGAATACTATCAGGCCATCACGGAGCCCCATCTCCA 8300

8301 GACCCATGATATGACGATTCAGGAGTACCGCGACGAGTACGGTGAGGATG 8350
         .gvpN>>>.
8351 TCCCCCTTCGGCCGGATGATAAAACATGACGAACGAGTCCCGTAAACGCA 8400
              ***gvpC
8401 AGGTACGAGGGTCGCAGATCCGCTCCTCACGCGGCGACAAGAAACAGGGG 8450

8451 CGATCACAGAGCCGTGATGATAAGGAGATCGAGCGTCTCGAGAGGCAGAA 8500

8501 CGACGCTCGTGGCCAGGAGTCGTCTACCCACGTCGACGAGGGGTTCGTTC 8550

8551 CCGAGGAACAGTCCTTCATCGAGACCGAATCGGTCAATCGAGTCGAGTCG 8600

8601 CGGATGGAACGGTGGCTCGATGTCGGACGTCCGGTTCACCTGATCGGGCC 8650

8651 GACCGGCTGTGGGAAAACGTCGCTGGCGATGCACGTCGCGCGCGAGCGCG 8700

8701 ATCGCCCGGTCGTCTGGATCAACGGCGACGCCGAACTCACGACCAGCGAT 8750

8751 CTCGTCGGCGAATACGCGGAAAAAGAGCGCATCTCGGAGCACGATCAATT 8800

8801 CATCCACAACGTCGTTAAGAGCAAGGACATCATCCGTGATCGATGGGTGG 8850

8851 ACAACCCCCTGACGCTCGCCGTACAAGAGGGGGCAACGCTGGTCTACAAC 8900

8901 GAGTTCTCCCGCACCAAGCCCGTCGCAAACAACGTGCTGTTGTCGGTCTT 8950

8951 CGAGGAAGGGGTGCTCGAACTGCCGGGGAAACGCGGCAAATCTCGGTATG 9000

9001 TAGATGTGCATCCTGAGTTCCGAACCATCCTGACCTCGAACTCCGTCGAG 9050

9051 TACGCTGGCGTCCACGAGCCGCAAGACGCCCTGCTCGACCGCCTCATCGG 9100

9101 GATCTACATGGATTTCTACGATCTCGACACGGAGATCGAGATCGTTCGGG 9150
```

FIG. 6I

```
9151 CGCACGTCGACAAGTCGGCCGACACAAACGTCGAGGACATCGTGCGGGTT 9200

9201 CTGCGTGAACTCCGCGAGCGGCTCGATATCACCGTGGGTACACGGGCCGC 9250

9251 GATTATGGCCAACGAAGGCGCTACCACCGTCGACACCGTCGACCAGGCCG 9300

9301 TCCTGACCGATATCTGTACCGACGTGCTGGCATCGAAGGTCGCCCAGCGG 9350

9351 AGCGACGTTCGCGGGCTGCGCGAAGAAATAGAATCCGCGATCGACGACAT 9400

9401 GGAAGTCGCCCTTTCTTAAGATCCGGGGTCTCTACATAGAAGCATGGCAG 9450
              ***gvpN
9451 ATCCAGCAAACGATCGATCTGAACGCGAGGAAGGCGGCGAGGACGACGAA 9500

9501 ACACCGCCAGCGTCCGACGGGAACCCCTCGCCGTCGGCCAATTCATTCAC 9550

9551 TCTCTCCAACGCGCAGACGCGCGCACGAGAGGCGGCACAGGACCTGTTGG 9600

9601 AACACCAGTTCGAGGGGATGATCAAAGCCGAGTCGAACGACGAAGGCTGG 9650

9651 CGGACCGTCGTCGAAGTCGTCGAACGGAACGCCGTACCCGATACACAAGA 9700

9701 CATCATCGGTCGCTACGAGATCACGCCTTGACGGGACGGGGACGTCACC 9750

9751 GGCTACGAGCTCCTAGAACGCTATCGTCGGGGCGACATGAAAGAGGAACT 9800

9801 GTAGCGGTGCGTCAAATGCACGAGCAATAGATATGGCCCATCGACTGACC 9850

9851 GTAGCGAACGAGAAAGGCGGCGTGGGGAAG 9880
```

RECOMBINANT VECTOR AND PROCESS FOR CELL FLOTATION

This is a continuation of application Ser. No. 08/271,270 filed on Jul. 6, 1994, now abandoned, by Shiladitya DasSarma, John Halladay, and Wai-lap Ng for RECOMBINANT VECTOR AND PROCESS FOR CELL FLOTATION, which is a continuation of application Ser. No. 07/944,581, filed Sep. 14, 1992, now abandoned.

This invention was made with United States government support under grant GM41890 awarded by the National Institutes of Health and grant DMB-8703486 awarded by the National Science Foundation. The United States government has certain rights in the invention.

FIELD OF THE INVENTION

Gas vesicles are bacterial organelles with a gas-filled cavity surrounded by a lipid-free proteinaceous membrane. These vesicles confer buoyancy to many prokaryotes. The present invention is directed to a recombinant vector capable of directing the synthesis of gas vesicles in non-floating cells. Cells transformed by the vector of the invention are also provided. The present invention is further directed to a method for conferring buoyancy to non-floating cells and a method of harvesting cells. The method of the instant invention is useful in harvesting cells, for example in fermentation processes, and in bioremediation, for example in conferring buoyancy to hydrocarbon-degrading bacteria.

BACKGROUND OF THE INVENTION

Gas vesicles are buoyant intracellular organelles found in many aquatic bacteria including halobacteria, cyanobacteria and methanogens. Gas vesicles have the form of central cylinders with conical end caps and are synthesized bidirectionally from the apices of the cones, with elongation proceeding by growth of the cylindrical region. The vesicle membrane is impermeable to water, and accumulation of gases in the vesicle interior is thought to be a consequence of passive diffusion of gases across the membrane and exclusion of water during the synthetic process. Accumulation of gas vesicles increases cell buoyancy and facilitates movement of cells to the surface of liquid cultures. For *Halobacterium halobium*, an aerobe with a photophosphorylation system utilizing the light-driven proton pump, bacteriorhodopsin, the consequence of gas vesicle accumulation is the increased availability of oxygen for respiration and light for photophosphorylation.

*H. halobium* contains two varieties of gas vesicles, a major type that is shorter and wider and a minor form that is longer, more slender, and observed in small amounts in cultures of gas vesicle defective mutants. *H. halobium* displays extreme genetic instability for the gas vesicle phenotype (Vac) apparent upon visual inspection of colonies on agar plates. Inflated gas vesicles diffract light, giving an opaque appearance to Vac$^+$ colonies, whereas Vac$^-$ mutants form translucent colonies. Spontaneous Vac$^-$ mutants are observed at a frequency of about 1%, and analysis of mutants has demonstrated that gas vesicle formation is determined or controlled by plasmid genes. Horne et al. (1988) *Mol. Gen. Genet*. 213, 459, have demonstrated that a plasmid gene encodes an 8.7 kD protein (GvpA, a constituent of the gas vesicle), and a chromosomal gene encodes a homologous 9 kD protein. The smaller plasmid encoded protein is constitutively produced in high amount while the chromosome encoded protein is produced only in the stationary phase, and probably accounts for the morphologically distinct gas vesicles observed in Vac$^-$ mutants.

Cloning of the major gas vesicle protein (GvpA)-encoding gene, gvpA, and analysis of Vac$^-$ mutants of *H. halobium* has resulted in the identification of a region of a 200-kb plasmid, pNRC100, which is important for gas vesicle synthesis. The nucleotide sequence of an 8520-bp region of pNRC100 has been reported which, including gvpA, contains a cluster of twelve genes organized into two divergent transcription units (Jones et al. [1991] *Gene* 102, 117, "Jones et al."). Analysis of spontaneously occurring mutants that are caused by the integration of insertion elements has suggested that several genes are involved in gas vesicle synthesis, but the role of the putative gene products in *H. halobium* is unclear.

Functional tests of cells transformed with vectors containing genomic DNA fragments of *H. halobium* have failed to identify the genetic information sufficient to direct gas vesicle formation. Blaseio et al. (1990) *Proc Natl. Acad. Sci*. 87, 6772 ("Blaseio et al."), have analyzed DNA fragments containing p-vac, a gene present on a 150-kb plasmid (pHH1) endogenous to *H. halobium*. The p-vac gene reportedly encodes a major structural protein of gas vesicles in *H. halobium*. *H. halobium* P03, a strain which lacks the p-vac region but contains a chromosomal c-vac, was transformed with a plasmid containing a 4.5-kb region of PHH1. The 4.5-kb region contained the entire p-vac region and 4-kb of flanking region. Transformants contained p-vac mRNA, but gas vesicles were not synthesized, indicating that expression of p-vac is not sufficient for gas vesicle formation. Blaseio et al. further report that transformation of *Haloferax volcanii* with a vector having an 11-kb fragment containing the mc-vac chromosomal gene from *Haloferax mediterranei* resulted in transformation to Vac$^+$ phenotype as measured by the presence of light refractile bodies under phase-contrast microscopy. There is no evidence that gas vesicles were synthesized, or that the transformed cells were capable of flotation. The phase bright-inclusions observed by phase-contrast microscopy are not evidence of gas vesicles, and could result from production of polyhydroxyalkanoates (Garcia-Lillo et al. [1990] *Applied and Environmental Microbiology* 56, 2517). Horne et al. (1991) *Mol. Microbiol*. 5, 1159 ("Horne et al.") report the transformation of Haloferax volcanii with the vector of Blaseio et al. modified by deletions in the mc-vac fragment. None of the transformed cells synthesized gas vesicles. Horne et al. further report that transformation of *Hf. volcanii* with a construct containing a 6.8-kb fragment of the *H. halobium* plasmid pHH1 containing the p-vac gene and significant amounts of flanking sequence failed to enable gas vesicle synthesis.

In accordance with the present invention, all of the genetic information necessary to direct the synthesis of gas vesicles has been identified. Furthermore, a method is provided for directing synthesis of gas vesicles in non-floating cells, and for transforming non-floating organisms to a floating phenotype.

SUMMARY OF THE INVENTION

The present invention is directed to a recombinant vector capable of directing the synthesis of gas vesicles in non-floating cells. More particularly, the present invention provides a vector containing DNA isolated from *Halobacterium halobium* wherein said DNA is operably linked to nucleotide sequences which effect expression of said DNA in a target cell and wherein said DNA encodes polypeptides capable of forming gas vesicles. In a preferred embodiment, said vector contains 13 genes designated qvpMLKJIHGFEDACN, or fragments thereof, derived from *H. halobium* plasmid pNRC100.

In another aspect of the invention, host cells transformed by the vector of the invention are provided.

A further aspect of the present invention is directed to a method for conferring buoyancy to non-floating cells.

A further aspect of the present invention provides a method of harvesting cells utilizing the buoyancy conferred to cells by the vectors of the present invention.

BRIEF DESCRIPTION OF THE DRAWINGS

FIG. 6 (Parts A–J) depicts the nucleotide sequence (SEQ ID NO: 1) of the gvp gene cluster and flanking DNA of pNRC100.

DETAILED DESCRIPTION OF THE INVENTION

The present invention relates to vectors which contain DNA which directs the synthesis of gas vesicles in non-floating cells. In particular, the vectors of the present invention are capable of directing the synthesis of gas vesicles in cells which do not contain gas vesicles. Gas vesicles, as defined herein, are cylindrical organelles with a gas-filled cavity surrounded by a proteinaceous membrane. Gas vesicles are known to one of ordinary skill in the art and are reviewed by Walsby et al. (1989) *Biochem. J.* 264, 313, for example.

It has been discovered in accordance with the present invention that vectors comprising DNA isolated from *H. halobium* and additional nucleotide sequences which effect expression of said DNA, including at least one promoter, direct the expression of gas vesicles in a host cell. In the present context, a host cell is any cell which does not contain gas vesicles prior to the introduction of the vector of the present invention and wherein said DNA is capable of being expressed in the host cell. The host cells can be, for example, bacteria or fungi.

According to the present invention, the subject vector includes DNA isolated from *H. halobium* wherein said DNA encodes the polypeptides necessary and sufficient for synthesis of gas vesicles under conditions appropriate to effect expression of said DNA in a target cell. *H. halobium* characteristically synthesize gas vesicles, and the gene (gvpA) encoding a major structural protein of gas vesicles maps to an *H. halobium* plasmid. The gvpA gene product alone, however, is not sufficient to direct the synthesis of gas vesicles. In accordance with the present invention, a cluster of genes associated with the gvpA gene has been discovered to encode the polypeptides which are required for gas vesicle synthesis. A gene cluster containing at least twelve genes, also designated the "gvp gene region", has been previously identified and partially characterized by DNA sequencing and transcription mapping (Jones et al., 1991). The gene cluster is located on a plasmid endogenous to wild type *H. halobium*.

In a preferred embodiment, the DNA encoding said polypeptides is isolated from plasmid pNRC100 of *H. halobium* strain NRC-1. With the teachings of the present invention, one of ordinary skill in the art can identify similar plasmids which naturally occur in *H. halobium* and which contain DNA encoding the polypeptides necessary for gas vesicle synthesis. Similar but nonidentical plasmids containing the gvp genes have been isolated from *H. halobium* (Blaseio et al., 1990; Jones et al., 1991). The similarity but lack of identity of the plasmids is likely to be the result of instability promoted by many repeated elements, including insertion sequences and inverted repeat sequences, which mediate recombinational activity.

Figure 1A:
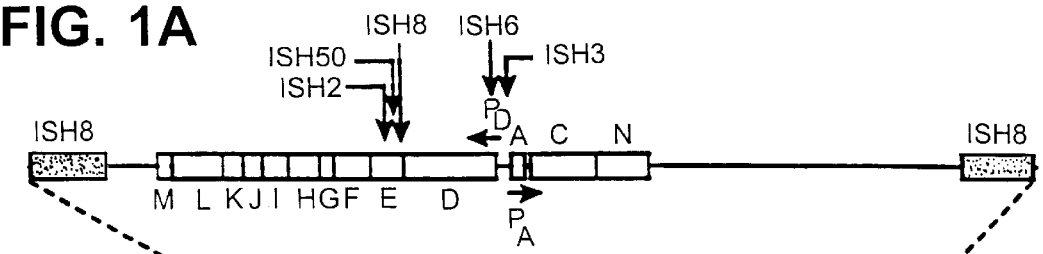
FIG. 1 (Parts A–B) depicts a physical and partial genetic map of plasmid pNRC100.
Figure 1B:
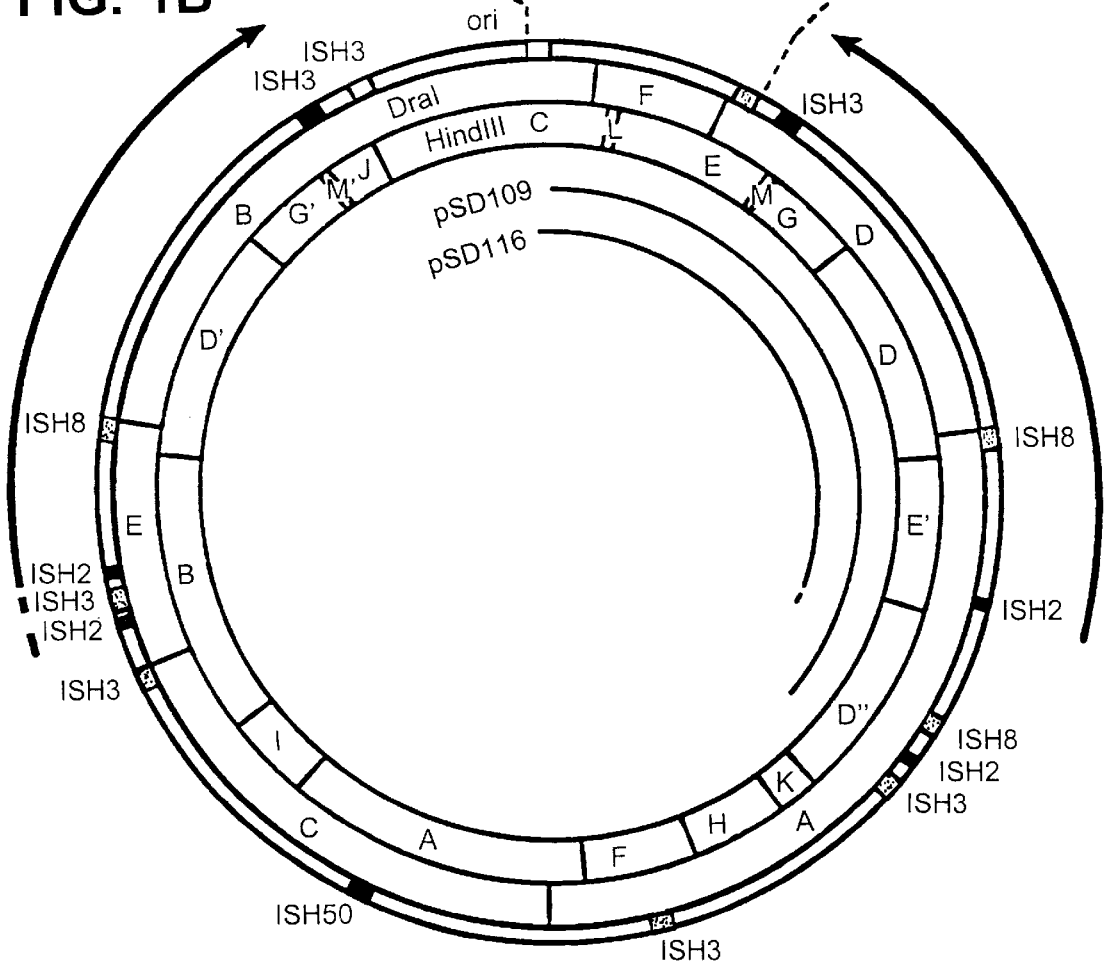

The 200-kb plasmid pNRC100 is a multicopy plasmid in *H. halobium* NRC-1 and has been characterized by Ng et al. (1991) *J. Bacteriol.* 173, 1958, ("Ng et al., 1991a") which is incorporated herein by reference. A physical and partial genetic map of plasmid pNRC100 is shown in FIG. 1. The plasmid contains many repeated elements, including at least seventeen copies of insertion sequence (IS) elements and a pair of very large inverted repeats (IR). In Part B of FIG. 1, the large inverted repeats are marked by heavy arrows and the IS elements are marked by shaded boxes. The ovp gene cluster, which contains the coding regions necessary for gas vesicle synthesis in accordance with the present invention, spans a 10–14 kb region bracketed by two ISH8 element copies in inverted orientation. ISH8 is a well-characterized 1.4 kb insertion sequence element described by DasSarma (1989) *Can J. Microbiol.* 35, 65.

The structure and organization of the gvp gene cluster of pNRC100 has been reported by Jones et al. (1991) *Gene* 102, 117, which is incorporated herein by reference. In accordance with the present invention, a thirteenth open reading frame, designated gvpN, has been identified. The thirteen genes are organized into two divergent transcription units, with the rightward unit containing gvpAC and N, and the leftward unit containing ten genes, gvpDEFGHIJKL and M. The genes are transcribed by divergent promoters, $P_A$ and $P_D$ located between gvpA and gvpD. Genes gvpAC and N are transcribed from $P_A$, and genes gvpDEFGHIJKL and M are transcribed from $P_D$. Part A of FIG. 1 indicates the relative sizes and positions of the gvp genes and the divergent promoters.

Jones et al. (1991) have reported the nucleotide sequence of an 8520 bp region of pNRC100 including leftward ISH8 terminal inverted repeat, the gvpA-M genes, and the $P_A$ and $P_D$ promoters. In accordance with the present invention, the nucleotide sequence of the gvpN gene is provided. The nucleotide sequence of the gvpN gene was determined by the method of Sanger et al. (1977) *Proc. Natl. Acad. Sci. USA* 74, 5463. The nucleotide sequence of the thirteen gvp genes and the $P_D$ and $P_A$ promoters of pNRC100 is set forth in FIG. 6.

FIG. 6 provides the nucleotide sequence (SEQ ID NO: 1) of a 9880-bp region of pNRC100 containing the thirteen gvp genes. The position of the ISH8 terminal repeat is indicated by a half arrow and the promoters $P_A$ and $P_D$ are indicated by large arrows. Each of the thirteen genes, gvpMLKJIHGFEDACN, is indicated. The positions of start codons (ATG) are indicated above the sequence by ">>>" and stop codons are indicated below by "***". The gene organization is highly compact, with the end of one open reading frame overlapping the beginning of the next in most cases.

To construct the vectors of the present invention, DNA encoding the polypeptides necessary for gas vesicle synthesis can be obtained as follows. Plasmid DNA can be isolated from wild type *H. halobium* NRC-1 by standard methods known to one of ordinary skill in the art as described, for example, by Pfeifer et al. (1981) *J. Bacteriol* 145, 375 and Ng et al. (1991b) in *Protocols for Archaebacterial Research*, Fleischmann et al., eds, University of Maryland, Baltimore, Maryland, 3.5.1–3.5.3 ("Ng et al., 1991b"). The isolation of the gvp gene cluster, or fragments thereof capable of encoding polypeptides necessary for gas vesicle synthesis, from plasmid DNA can be accomplished by restriction endonuclease digestion as taught, for example, by Sambrook et al. (1989) *Molecular Cloning, A Laboratory Manual*, Cold Spring Harbor Laboratory Press, Cold Spring Harbor, New York, or by other art recognized methods, including but not limited to chemical or enzymatic synthesis based upon the nucleotide sequence of the gvp genes designated SEQ ID NO: 1 and set forth in FIG. 6.

In a preferred embodiment, the region between the two ISH8 elements as depicted in FIG. 1 is isolated from plasmid pNRC100 by restriction endonuclease digestion. The region can be isolated as multiple restriction fragments and then reconstructed by standard methods known to one of ordinary skill in the art and taught, for example, by Sambrook et al. (1989). The ordinarily skilled artisan can determine, by wellknown methods such as deletion analysis and insertion mutagenesis, the minimum sequence or part of the gvp gene cluster between the two ISH8 elements which is required to allow function in the context of the vectors of the present invention, i.e. to direct synthesis of gas vesicles in nonfloating cells. The ordinarily skilled artisan can determine the minimum part of the gene cluster required to maintain function by transforming target cells and determining the formation of gas vesicles by electron microscopy or by visually determining the ability of transformed cells to float. Suitable assays are described hereinbelow. The skilled artisan can similarly determine which minor modification of the sequence can be tolerated while maintaining function.

In a preferred embodiment, the DNA encoding polypeptides necessary for gas vesicle synthesis comprises the genes gvpMLKJIHGFEDACN as set forth in FIG. 6 (SEQ ID NO: 1). The ordinarily skilled artisan can determine which of the genes gvpMLKJIHGFEDACN and which fragments thereof are sufficient for directing formation of gas vesicles by preparing vectors containing the genes or fragments thereof, transforming cells and assaying for the formation of gas vesicles and ability of transformed cells to float. For example, comparison of deduced amino acid sequences for GvpA, GvpJ and GvpM, indicates that the gene products are related small acidic proteins with molecular sizes ranging from 8–12 kDa (Jones et al., 1991). The skilled artisan can determine, by methods described above, the criticality of any or all of such related proteins for gas vesicle synthesis in a particular host cell.

Similarly, the entire coding region of a gvp gene may not be required to effect gas vesicle synthesis in a transformed host cell. The skilled artisan can determine which deletions or modifications of the gvp genes can be tolerated while maintaining function. For example, gvpD, E, F, G, H, I, J, K, L and M each contain sequences positioned 7–12 bp upstream from the putative ATG start codons which are complementary to sequences ear the 3' end of the *H. halobium* 16S rRNA (Jones et al., 1991). Such sequences are known to function as ribosomal binding sites in prokaryotic translation systems, but may not be absolutely required for efficient translation. Further, as discussed below, the *H. halobium* ribosomal binding sequences may be replaced by sequences which function as ribosomal binding sites in a particular host cell.

The DNA isolated from *H. halobium* and capable of encoding polypeptides which form a gas vesicle is obtained as described above, and placed within replicable expression vectors. Replicable expression vectors as described herein are DNA or RNA molecules engineered for controlled expression of a desired gene or genes, i.e. the genes which direct the synthesis of gas vesicles. Such vectors also contain nucleic acid sequences which effect expression of the genes which encode the gas vesicle polypeptides. The nucleic acid sequences include promoters and other sequence elements which can control gene expression, and an origin of replication which is operable in the contemplated host cell. Preferably the vectors are plasmids, bacteriophages, cosmids or viruses. Sambrook et al. (1989); Goeddel, ed. (1990) *Methods in Enzymology* 185; Perbal (1988) *A Practical Guide to Molecular Cloning*, John Wiley and Sons, Inc.; and Romanos et al. (1992) *Yeast* 8, 423–488 provide detailed reviews of vectors into which the DNA which encodes the gas vesicle components can be inserted and expressed. Shuttle vectors, which contain origins of replication active both in *E. coli* and in another target organism, are particularly preferred. Shuttle vectors allow amplification and manipulation in *E. coli* before transformation of a target cell.

Sequence elements capable of effecting expression of a gene product include promoters, enhancer elements, upstream activating elements, transcription termination signals, ribosome binding sites, splicing signals and polyadenylation sites. All such transcriptional and translational regulatory elements, singly or in combination, are contemplated for use in the present replicable expression vectors. Moreover, genetically engineered and mutated regulatory sequences are also contemplated.

Promoters are DNA sequence elements for controlling gene expression. In particular, promoters specify transcription initiation sites and can include a TATA box and upstream promoter elements. In accordance with the present invention, bidirectional promoters are preferred. Bidirectional prokaryotic promoters that are useful in the vectors of the present invention include the $P_A$ and $P_D$ promoters of PNRC100 of *H. halobium*, the $P_R/P_{RM}$ promoters of lambda, and the $P_L$ and $P_R$ promoters of lambda. Other prokaryotic promoters, for example the lac, trp, and trp-lac promoters from *E. coli*, the bacteriophage T7 polymerase, T3 polymerase and SP6 polymerase promoters and related prokaryotic promoters are also contemplated. Sambrook et al. (1989) and Goeddel (1990) also review prokaryotic promoters which are useful in the present invention.

For constructing vectors to transform yeast cells, sequence elements which effect expression in yeast are used. Birectional promoters useful in yeast expression systems are the GAL1/GAL10 divergent promoter, and viral promoters which function in eukaryotic expression systems, such as the SV40 promoter. Other yeast promoters that are useful in the vectors of the present invention include the GAL1, PGK, GAP, TPI, CYC1, ADH2, PHO5, CUP1, MFα1 and related promoters. Romanos et al. provide a review of yeast promoters. Foreign promoters not recognized by yeast RNA polymerase can be used if the cognate RNA polymerase is co-expressed.

The expression vectors of the present invention intended for use in prokaryotes may contain the ribosomal binding sites from the *H. halobium* DNA or, alternately, another ribosomal binding site suitable for a prokaryotic host. Ribosomal binding sites include an initiation codon and a Shine-Dalgarno sequence which are optimally spaced for efficient expression. Such an optimal spacing is known to the skilled artisan and can be about 3–20 nucleotides.

Yeast mRNAs do not appear to require a ribosomal binding site to mediate the general mechanism of translation. However, optimal initiator regions surrounding the start codon are known to the skilled artisan and can be found in Kozak (1986) *Cell* 44, 283; Cigan et al. (1987) *Gene* 59, 1; and Goeddel (1990). The use of elements encoding yeast consensus start regions is contemplated in the vectors of the present invention which are intended for use in yeast.

One skilled in the art can readily design and make replicable expression vectors which include the above-described elements by combining DNA fragments from available vectors, by synthesizing nucleic acids encoding such regulatory elements or by cloning and inserting new regulatory elements into known vectors. Methods for constructing expression vectors are wellknown. Recombinant DNA methods can be found in any of the myriad of standard laboratory manuals on genetic engineering (Sambrook et al. [1989]; Goeddel [1990]; and Romanos et al. [1992]).

The vectors of the present invention can be constructed by ligating the DNA encoding the polypeptides necessary for gas vesicle synthesis in the proper orientation to the promoters and other sequence elements which effect gene expression. The proper orientation is defined as the arrangement of coding regions, promoters and other sequence elements which results in efficient transcription and translation. In a preferred embodiment, the orientation of the genes of the gvp gene cluster and the promoters mimic the orientation in the naturally occurring pNRC100 plasmid as shown in FIG. 1. In other words, the thirteen genes or fragments thereof are organized into two divergent transcription units, with the rightward unit containing gvpAc and N, and the leftward unit containing ten genes, gvpDEFGHIJKL and M. The genes are transcribed by divergent, i.e. bidirectional, promoters appropriate for the target cell and located between gvpA and gvpD. In another preferred embodiment, the gvp transcriptional units are inverted relative to the orientation in pNRC100 and are flanked by a promoter at each end such that transcription is directed inward, and suitable termination sequences are provided between the two transcriptional units. In another embodiment, the promoters and coding sequences are arranged in tandem, i.e. promoter-coding region-promoter-coding region. In yet another embodiment, the coding regions and respective promoters can be contained on two or more distinct vectors which can be co-expressed in the target cell. In a preferred embodiment, the vector of the present invention contains a rightward transcription unit including gvpAC and N and a leftward transcription unit including gvpDEFGHIJKL and M wherein a bidirectional promoter appropriate to effect expression of the gvp genes in a host cell is inserted between the two transcriptional units.

In accordance with the present invention, a 31-kb *H. halobium-E. coli* shuttle vector containing the region located between the two ISH8 elements of pNRC100 comprising the gvp gene cluster is provided. In addition to being capable of directing the synthesis of gas vesicles in non-floating bacterial cells, as described hereinbelow, the subject shuttle vector can serve as a basis for construction of other vectors of the present invention, for example, by deleting or adding regions, or by substituting promoters or other regulatory elements. The shuttle vector is designated pJHGV3 and is able to replicate in both *E. coli* and *H. halobium*. Plasmid pJHGV3 contains the entire gvp gene cluster flanked by the two ISH8 elements. Details of the construction of pJHGV3 are provided in Example 1 and depicted in FIG. 2.

In another aspect of the present invention, the vectors of the present invention are introduced into a host cell. Any prokaryotic or eukaryotic cell having a non-floating phenotype is contemplated as a host cell. In accordance with the present invention, *E. coli* and related enteric bacteria useful for the synthesis of recombinant products are contemplated as host cells. Pseudomonads and other related nutritionally diverse organisms useful for bioremediation are contemplated as host cells. Other host cells in accordance with the present invention are fungi, for example Aspergillis, and especially fungi which produce antibiotics and pharmaceutical compounds, and yeasts, for example *Saccharomyces cerevisiae* and *Schizosaccharomyces pombe*. Mammalian cells grown in suspension culture, such as lymphocytes for production of lymphokines and interferons, are also contemplated as host cells. Bacteria and yeast are particularly preferred. In accordance with the teachings of the present invention, the ordinarily skilled artisan can construct vectors suitable for transformation of and expression in a particular host cell. For example, vectors comprising promoters and other sequences to effect transcription and translation in yeast, which are known to the ordinarily skilled artisan and described hereinabove, are used for transformation of yeast, and vectors containing appropriate promoters and other sequences to effect expression in bacteria are used for transformation of bacteria.

Methods of transformation are known to one of ordinary skill in the art. Methods for transformation of bacterial cells are reviewed by Sambrook et al. (1989) and methods of transformation of yeast cells are provided by Romanos et al. (1992).

The functionality of the vectors of the present invention is assessed by determining the ability of cells transformed by the present vectors to float. Transformed cells are grown in appropriate liquid culture and visually assessed for their ability to float. The presence of gas vesicles in transformed cells results in spontaneous flotation, which can be accelerated by low speed centrifugation. Wild type *H. halobium*, which float in liquid culture, and Vac⁻ mutants or other non-floating cells, which sediment in liquid culture, can be used as a positive and negative controls, respectively. To verify that the ability of transformed cells to float is a result of the production of gas vesicles, gas vesicles are partially purified from transformed cells and compared to wild type vesicles by negative staining and electron microscopy. Gas vesicles can be partially purified by flotation (overnight centrifugation at 60×g) after lysing confluent cell cultures, for example as described by Krantz et al. (1973) *J. Bacteriol.* 114, 1058.

A further aspect of the present invention is directed to a method for conferring buoyancy to non-floating cells. The method comprises transforming a non-floating cell with a vector of the present invention. The method and transformed cells of the present invention are useful in bioremediation. For example, by transforming hydrocarbon-degrading bacteria with the vector of the present invention, buoyancy is conferred to said bacteria, thus enabling the bacteria to be maintained on the surface of an aqueous liquid, for example, at an oil-water interface.

The present invention also provides a method of harvesting cells. The method includes transforming non-floating cells with the vector of the present invention, allowing the transformed cells to float in aqueous medium, and separating the transformed cells from the medium, for example by skimming or decanting.

The method and transformed cells of the present invention are useful in any method which requires harvesting of cells from a liquid medium, for example in fermentation processes and cell culture. For example, many recombinant products, such as lymphokines and interferons, are produced by mammalian cells which are grown in suspension. The ability of the transformed cells to float allows harvesting by skimming from the surface or by decanting rather than by filtration or centrifugation.

The following examples further illustrate the present invention.

EXAMPLE 1
Construction of an *H. halobium-E. coli* shuttle plasmid

Figure 2:
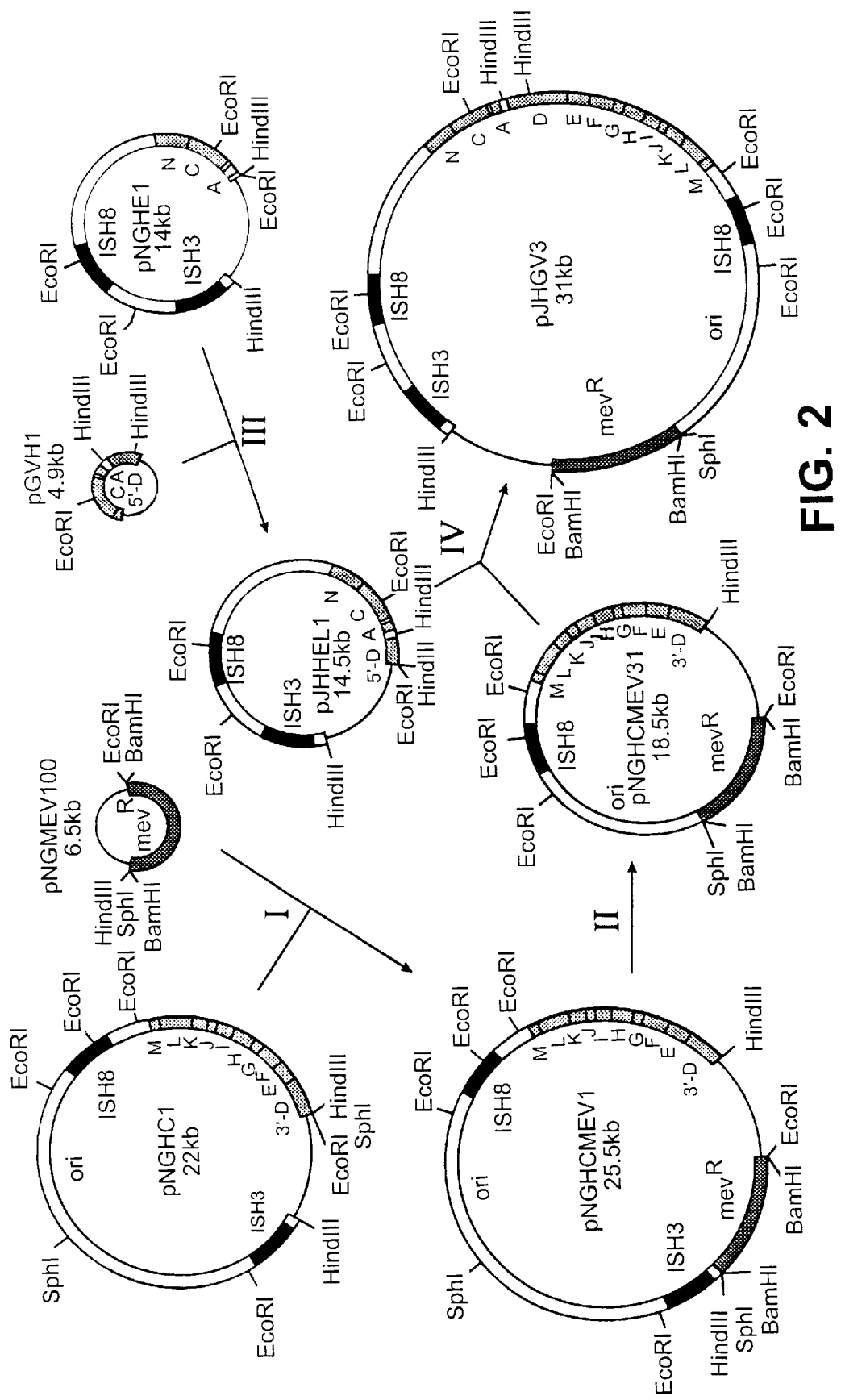
FIG. 2 diagrams the construction of pJHGV3, a 31-kb *H. halobium-E. coli* shuttle vector containing the gvp gene cluster.

The gvpA gene cluster spans a 10–14 kb region of the *H. halobium* plasmid pNRC100 located between two ISH8 elements (Jones et al. 1991; Ng et al., 1991a). Since no appropriate restriction fragment containing the entire cluster could be identified, the region was isolated as three HindIII fragments, a 19-kb fragment (HindIII-C) containing the 3'-end of gvpD and gvpEFGHIJKL and M, a 0.7-kb fragment (HindIII-L) containing the 5'-end of gvpD and the promoter region of the leftward transcription unit, and an 11-kb fragment (HindIII-E) containing the gvpA promoter and structural gene, gvpC and gvpN, and cloned into pUC12 or pTZ19R (Vieira et al [1982] *Gene* 19, 259). A 12-kb subfragment of HindIII-C contained an ori, as shown by its ability for autonomous replication in *H. halobium* when inserted into an *E. coli* recombinant plasmid containing a mevinolin resistance (mev$^R$) marker from the related halophile *Haloferax volcanli* (Lam et al [1989] *Proc. Natl. Acad. Sci. USA.* 86, 5478) (FIG. 2, steps I–II). This *H. halobium-E. coli* shuttle vector, pNGHCMEV31, confers Mev$^R$ when transformed into *H. halobium* and ampicillin resistance (Ap$^R$) in *E. coli*. Next, the HindIII-L fragment was inserted into plasmid pNGHE1 which contains the 11-kb HindIII-E fragment to form pJHHEL1 (step III) followed by excising HindIII-L and E together as a single fragment by partial digestion and inserting it into the HindIII site of pNGHCMEV31 to form pJHGV3 (step IV). Plasmid pJHGV3 is able to replicate in both *H. halobium* and *E. coli* and contains the entire gvpA gene cluster flanked by the two ISH8 elements.

Further details of the construction of the shuttle plasmid are as follows. The indicated steps refer to FIG. 2.

Step 1: The HindIII-C fragment of pNRC100 (containing the 3'-end of gvpD and gvpEFGHIJKL and M) cloned in pTZ19R (pNGHC1) was recovered with HindIII and cloned into the HindIII site of pNGMEV100, which had been constructed by inserting a 3.5-kb KpnI-SphI fragment containing the mev$^R$ gene from *Hf. volcanii* (Lam et al., 1989) using BamHI linkers into the BamHI site of pTZ19R. The resulting plasmid pNGHCMEV1 was used for DNA-mediated transformation of *H. halobium* to Mev$^R$, indicating that it contains a pNRC100 ori. Step II: A 7-kb HindIII-SphI fragment not essential for gas vesicle synthesis or replication was deleted from pNGHCMEV1 by digestion with SphI, gel purification of the 18.5-kb fragment, and self-ligation in order to construct pNGHCMEV31. Step III: The HindIII-E fragment of pNRC100 (containing gvpAC and N and the downstream region) cloned in pTZ19R (PNGHE1) was linearized by partial digestion with HindIII, and ligated with a gel purified HindIII-L fragment of pNRC100 (containing the 5'-end of gvpD) from pGVH1, the original gvpA gene clone, to form pJHHEL1. Step IV: A 12-kb HindIII fragment (HindIII-L+E) generated by partial HindIII digestion of pJHHEL1 was inserted into the HindIII site of pNGHCMEV31 to reconstruct the entire gvpA gene cluster in pJHGV3. Standard recombinant DNA procedures were followed and constructs were characterized by restriction mapping. The gvP genes (labelled A–N) are shaded as is the Mev$^R$ gene. The IS elements are shown as black boxes and the *E. coli* pUC12 and pTZ19R vector portions are shown as simple lines. The approximate position of the plasmid pNRC100 ori is indicated.

EXAMPLE 2
Transformation of *H. halobium*

Plasmid pJHGV3 (FIG. 2) was amplified in *E. coli* and used to transform two *H. halobium* Vac mutants, SD109 and SD116. These two strains have been shown to be deleted for the entire gvpA gene cluster (DasSarma et al., [1988] *Proc. Natl. Acad. Sci. USA* 85, 6861; DasSarma, [1989]) with the deletions extending from the ISH8 element located beyond the left end of the gene cluster to the HindIII-D" fragment (FIG. 1). SD109 and SD116 were transformed with pJHGV3 using the EDTA-PEG procedure of Cline et al. (1987) *J. Bacteriol.* 169, 1341. The transformed cells were then spun down, resuspended in *H. halobium* medium and allowed to regenerate for three days at 37° C. with shaking, and plated on agar plates containing 10 μg Mev per ml. Colonies of *H. halobium* SD109 and SD116 transformants exhibited a significantly increased opacity (Vac$^+$ phenotype).

Figure 3:
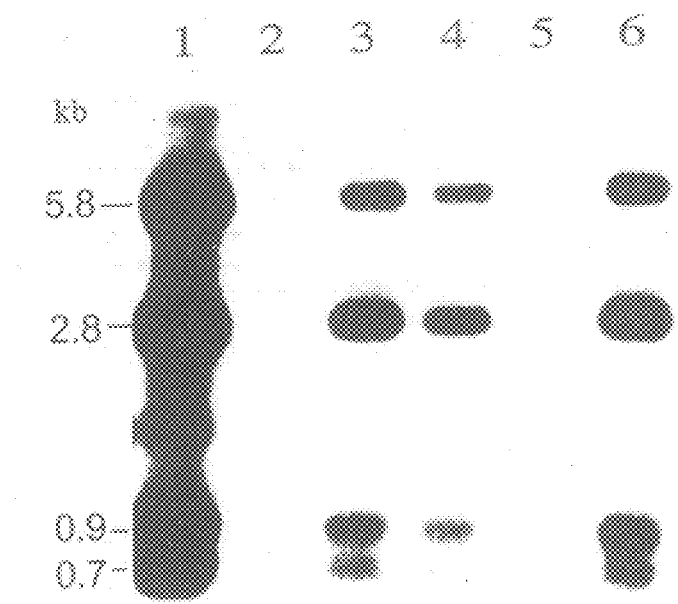
FIG. 3 demonstrates the presence of restriction fragments of pJHGV3 in transformed cells by Southern analysis.

Two Vac$^+$ transformants of each strain, SD109-7 and -8 and SD116-7 and -8, were selected for further analysis. Initially, plasmid DNA was isolated (Ng et al., 1991b) from each transformant as well as the untransformed strains and compared to the transforming plasmid pJHGV3 DNA isolated from *E. coli* by Southern analysis with pGVH1 labeled with $^{32}$p by nick translation (FIG. 3).(DasSarma et al., 1987). pGVH1 is a clone containing a 2.2 kb Sau3A fragment of pNRC100 including gvpA and C and flanking regions. Plasmid DNA from *E. coli* DH5α(pJHGV3) (lane 1), *H. halobium* SD109 (lane 2) and SD116 (lane 5), two Vac$^-$ mutants with deletions of the entire gvpA gene cluster, and Vac$^+$ transformants SD109-7 (lane 3), SD109-8 (lane 4), and SD116-7 (lane 6) were digested with HindIII and EcoRI and analyzed by Southern hybridization using pGVH1 $^{32}$p labelled by nick translation as a probe. Sizes of major hybridizing fragments are shown.

The EcoRI-HindIII restriction fragments of pJHGV3 probed by pGVH1 (lane 1) are present in each of the transformants (lanes 3, 4, and 6, data not shown for SD116-8), indicating that they contain pJHGV3 as an extrachromosomal replicon. The untransformed Vac$^-$ strains (lanes 2 and 5) exhibited only weak hybridization to the gvpB gene cluster.

EXAMPLE 3
Analysis of Induction of Flotation by Transformation with pJHGV3

Figure 4:
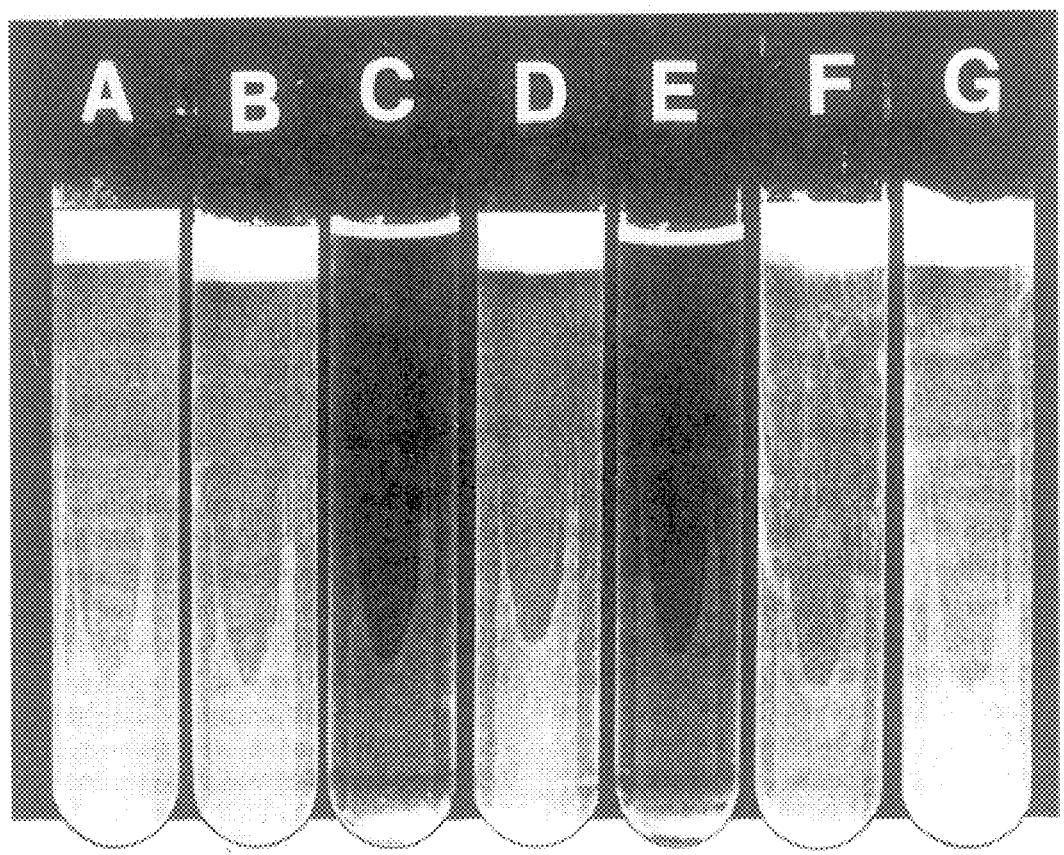
FIG. 4 demonstrates the ability of transformed cells to float in liquid culture.

Liquid cultures of SD109-7 and -8 and SD116-7 and -8 were grown to stationary phase and analyzed for the ability of cells to float. Five ml. cultures of approximately $10^8$–$10^9$ cells were assessed in glass test tubes. As shown in FIG. 4, the transformants have essentially wild type ability to float in contrast to the observed sedimentation of the Vac$^-$ untransformed cells (compare transformant cultures A, B, F, and G to wild type culture D and Vac$^-$ mutant cultures C and E).

In FIG. 4, tube D contains a culture of the wild type strain NRC-1 and tubes C and E contain Vac$^-$ strains, SD109 and SD116, respectively, deleted for the entire gas vesicle gene region. Tubes A, B, F, and G contain Vac$^-$ mutant strains, SD109-7, SD109-8, SD116-7, and SD116-8, respectively, transformed with pJHGV3, the gas vesicle gene shuttle plasmid. Floating Vac$^+$ cells are visible as a pink band at the surface, and cells that sink (Vac$^-$) are visible at the bottom of the tube as a red pellet. The meniscus is visible in tubes C and E.

Figures 5A, 5B, 5C:
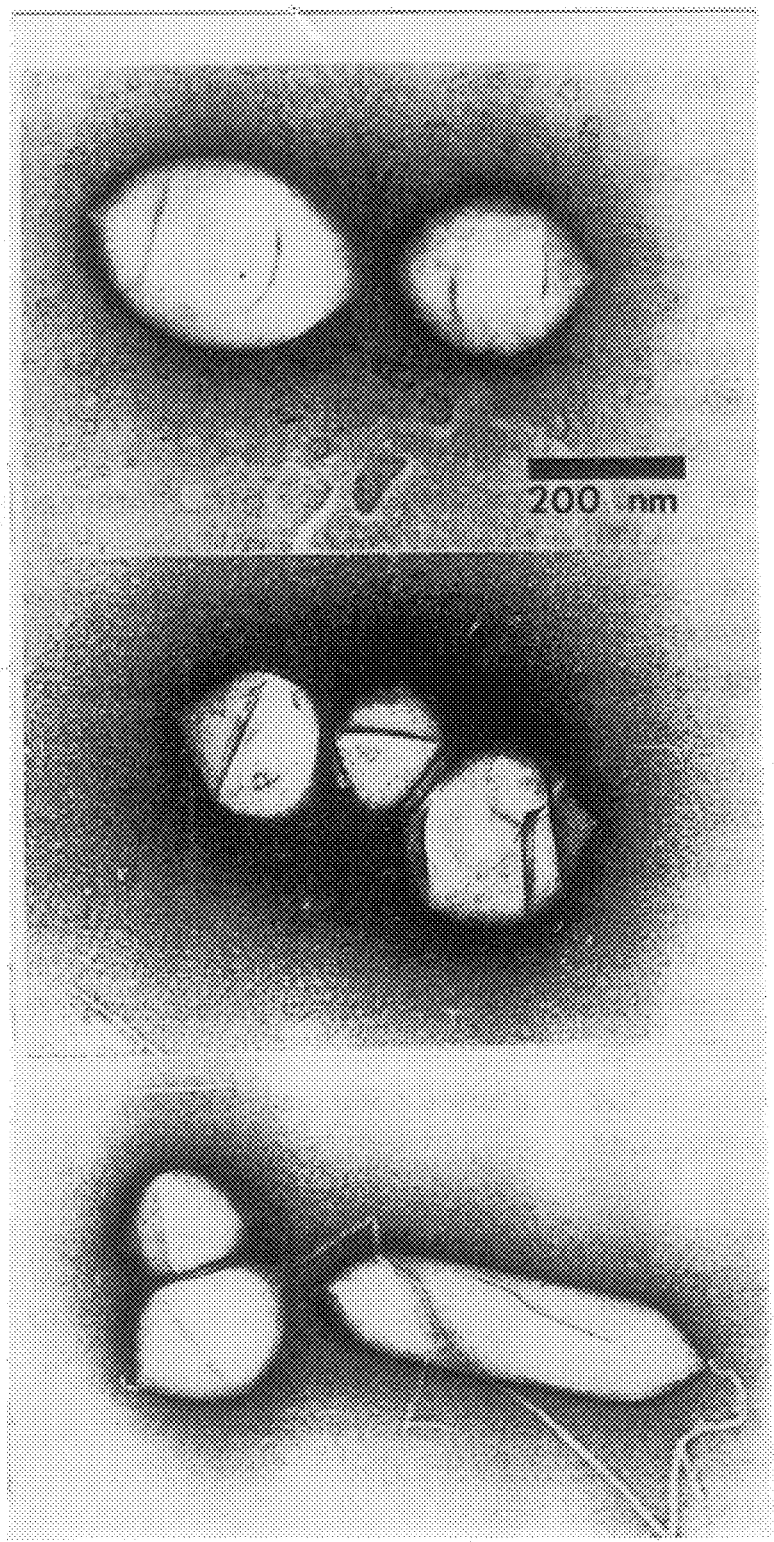
FIG. 5 (Parts A–C) is an electron micrograph of gas vesicles purified from wild type *H. halobium* NRC-1 and Vac⁻ mutants transformed with pJHGV3.

In order to examine the morphology of the gas vesicles produced in the transformants, gas vesicles were partially purified from SD109-8 and SD116-7 by flotation and compared to wild type vesicles by negative staining in the electron microscope. Gas vesicles were purified from lysates of *H. halobium* NRC-1 (FIG. 5A) and transformants SD109-8 (FIG. 5B) and SD116-7 (FIG. 5C) by flotation at 60×g overnight. The vesicle preparations were negatively stained with uranyl acetate and examined by transmission electron microscopy. The morphology of vesicles in the transformants is essentially wild type with the presence of both the abundant wider type and the rare slender vesicles (FIG. 5). No vesicles could be observed in the untransformed Vac⁻ strains subjected to similar analysis.

---

What is claimed:

1. An expression vector which directs the production of gas vesicles in *E. coli*, said vector comprising genes encoding *Halobacterium halobium* proteins required for the synthesis of gas vesicles in *E. coli*, said genes being operably linked to nucleic acid sequences which direct the expression of said genes in *E. coli*.

2. The expression vector of claim 1 wherein said vector encodes gvpA, gvpC, gvpN, gvpD, gvpE, gvpF, gvpG, gvpH, gvpJ, gvpL, gvpM, gvpK, and gvpI.

3. *E. coli* harboring the expression vector of claim 1.

4. A method of increasing the buoyancy of an *E. coli* cell, comprising:
   transforming said *E. coli* cell with an expression vector which directs the production of gas vesicles in said *E. coli* cell, said vector comprising genes encoding *Halobacterium halobium* proteins required for the synthesis of gas vesicles in *E. coli*, said genes being operably linked to nucleic acid sequences which direct the expression of said genes in *E. coli*,
   culturing said *E. coli* cell under conditions which permit production of said gas vesicles, wherein production of said gas vesicles increases the buoyancy of said cell.

5. The method of claim 4 wherein said vector encodes gvpA, gvpC, gvpN, gvpD, gvpE, gvpF, gvpG, gvpH, gvpJ, gvpL, gvpM, gvpK, and gvpI.

6. *E. coli* harboring genes encoding *Halobacterium halobium* required for the synthesis of gas vesicles in *E. coli*, said genes being operably linked to nucleic acid sequences which direct the expression of said genes in *E. coli*.

7. The *E. coli* of claim 6 wherein said genes encode gvpA, gvpC, gvpN, gvpD, gvpE, gvpF, gvpG, gvpH, gvpJ, gvpL, gvpM, gvpK, and gvpI.

8. A method of increasing the buoyancy of an *E. coli* cell, comprising:
   transforming said *E. coli* cell with DNA which directs the production of gas vesicles in said *E. coli* cell, said DNA comprising genes encoding *Halobacterium halobium* proteins required for the synthesis of gas vesicles in *E. coli*, said genes being operably linked to nucleic acid sequences which direct the expression of said genes in *E. coli*,
   culturing said *E. coli* cell under conditions which permit production of said gas vesicles, wherein production of said gas vesicles increases the buoyancy of said cell.

9. The method of claim 8 wherein said genes encode gvpA, gvpC, gvpN, gvpD, gvpE, gvpF, gvpG, gvpH, gvpJ, gvpL, gvpM, gvpK, and gvpI.

\* \* \* \* \*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 9880 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GTGAGTCTTA ACTGAAGACG AATGCCGTGT CGGGATTGAG CGAGCAGAAA CGCACCTCAC      60

GGACTCCGAA GTCCAGGAGA AGACCTCCTA TGACGGGAAC GTGGATCAGA TCGAGACCTG     120

CATCGTTTAC GATGGAATCG ACGAGGAATA CCTCGAGAAG TGCCGGAACG AATGGGACAA     180

CTGCCGGGAA AAGCTAGAGA AACTCGAAGA ACAAACCGCC ATCCTCACAC AGGGACATGG     240

AGAGTCATTG CGGTTGCTCA CTGGAGAGTT CGACTCTACT CGACTACAAT CCCGCTTCGA     300

GAGCGGTATC GATCTCCCGG TGAATCCGAA GACAGAGTTC GTCGCTGCCG TCCCCGGCAG     360

TGGGCTCGTC GAAAGACGCC GAACCCGATC CGGAACGACT CCGATCAGCG AGAACAGTGG     420

TCTTGCCCGT CCTGTCACCG AAAATTTCGC TCACACCGCG GGTTACAGCG CCACTACGAC     480

ACCAACCGCG AACACGCGGA GGCGATGATC GACGTCGATC GGGAACTGGA GCAGGATGAG     540

AGTACCAGCG CCGGAACTGA ATGGGTCGAG TTCGTCGACC AGATTGAGAC GTTCTGTAAA     600

CTCTCGGATG GATTCGACGA GAGTGAGATC ACCGTCACGC ACGATTCAGC TACCCACTGC     660

GTCCGTATCT CCGGCGCACA CGAGAATTCA ATCGATACGA GTCCCGTCTC CGAGACGATC     720

GACGGCGACG TGGAGTGGCG TTCGTCTGGA CGCTACCTTG TCCTCTCGTT CCCGCTGTGA     780

ACCGGTGGTC TTTCGCCTCG CCACCGCTGT GATTCAACAT ATCCCAGTTG GGTTTCCGCA     840

TTATCCCTCT CCTTTATTCT CACGCGACAC GACCTCGAAT CAGTCCTCTC GCCGATCGGC     900

AGTGGGCGAG GTCGTGAACG CTTCGCTCTG TTGTCGATGC GCAGCATCCC ACTCCTCGAA     960

CAGGCCGTAC TCCGTCATGG TGGTCATGCC AGCAATCGCT GCCCGGAGGC TGATCCCGAT    1020

CAGGGGAATG TCGGCGACCG TCACGATCAC GTCCGCTTGA ATCACGGCTC CGTCGCGCAG    1080

TAACACGTCG ACGAACTCAA CGATCGCGTG TGTCTCGTCT TTTGTTGGCT CCATTATTTA    1140

CCAATATCTG GCGCGAACGT GTACGGTGGC CACGGCCCCG TGAATCTGAT CTCTACACCC    1200

TCGTGTTCGA CGATCGTATC CAATCGATCA CCGAGAGCGG TCTCGTCGTC CTCGTCCGCG    1260

AGAACGGCGA ACCGCACGAT CTGTTCTTTC TCGATGGACG AGTGTTCGTC CTGTAGCGGC    1320

GTATTCGTGT CCTGTTCGGT CAGGTCGTTC ACGACCGGGG TAATGCCCTC TTTCAGTTGA    1380

TCTGCTAGTT CCGTCCGGCG CTCTCGTTTC AGCTCTTGGA GTCGCTGATC GGACTGTTTC    1440

TCGAGGAGGA ACTTTTTCCC TGCGCCCGAT TGTTGCTGGC GCTGTCGTAG TTCTCGGAGC    1500
```

-continued

```
CGGTCGTCTC GGTCTGCGAT GGTCTCCTCG AACGGTGCGG AATCCCACAA CAGATTGATT    1560

CGATACTCCC ACACTCCCGC GAACGACGCT AATTCGTCGC GGAAGCCCTC GTAGTGGTCT    1620

TCTAACCACC GTTCGATACT CGCATCACCG CCCTCGAGGA CCGTGTCGAA TCGCATCGGC    1680

AGCGGCGTAC CGAACGCGTC GCTCGCCGCG TCGACGACCT GCTGGTGCGT GACCAGCCAT    1740

CGCTTCACCT GTTCGAGGTC TTCCGTCTCG TAGACCGTCT CACAGTCATG GACGACGGCG    1800

CCCACGCCAT CGGCCTCGAC GACGTAGACA GGGTTGTCGT CGACCCCGGT CGTGGACAGG    1860

GTCGCCGATT CCGACGACGT GGTATCGACC ACGCAGTATA GATAGCGGCC GTTGCTGACC    1920

GTCCGTTCCT CGTTCGCTGT GGTCTGCTCT TCTTCCGGGC TGGGCCGGTG GTCAGTCATA    1980

CGTCATCACG CTGGGATTCC GGCGAGCCGT GACCTGACGG TGTCTCGTGC TCGGATAGCT    2040

GTTCGATGGC GTCGCGGATC ACGTGATCGA GGTCCTCCCT AAACTCGGAG ACCTCGGCGT    2100

TGATATCCTC TTGCTGTTTC AGTCGCTCGA GCTCGTCTTC GAGGGCCTGT AATTGTCGCC    2160

CCAATCGTTC GATTTCGTCC TCTGAGAGCG ACCCGGATTC CATCCGACGC ACCGCTTCTT    2220

GTTCGAGGGC CTCGACCAGC AATTCGACGA CAGTTACGAC CAGCGCCGTG AGCCCGCCTT    2280

GCAAATCGTC CGCGTCGTCG TCGAGTGCTA GTTCCATCTC ATTTGGTCTC CTCCGCTGAC    2340

GTGGATGCCG TCGGCGTCGA ATCGTCCGAC AGTGGGTTCG TCGACTCGGT CTCCGATTGG    2400

GTTTCCGACG CCGGGTCGGA CTGGTCCGGT GAGATATTCG CGGCGGACTC GACGCGCTCC    2460

ATATCCGTCC CCGTTGGGAA CTCGAGCCCG TATTCGGCCG CTGTCTCGAA CGAAGCAATC    2520

GCGGCCCGTA ACTCGATACC GAGGAGTTCC GTGTCCCCGA CGCTGACTGC GATATCCGCG    2580

TTGACGACGA CTCCTTTGTC TAGGAGCATC TCCAGCATCT CGGCGAGGTC GCCCTGCGAG    2640

CGCGTCGGTT TGGGGTCACT CATCGTTCAC CTCGTCCTCA GTGGGACTCC CGGACGCGCT    2700

CTCATCCGAC GGGGCGGATG CCTCCGAGTT TCCACCGGCT GTTTTCTGGT GAAGCCGTTG    2760

GCCGTACAAT CGCTCTCGAG CCGTCACATC CGAGTACTTC GGAGTCTTCG GGACGGTCGA    2820

GTGGGAGTTG CGTACCGCGT TCTCCGCGTT CGACTTCTGA GGCGGCATCG TCGAGTGAGC    2880

CGCTGGATTC TTGACCGTCT CCCCGTCAGT ATCGTCGCCG TCGGAATCGT CACGCCGGGG    2940

TTCCGACTGT TTCCGGTTGC GGGTCCGACG CCGGGCGAGT TTTTCGCGCT GCCGAAGCAG    3000

ATTGCGCCGG GCTTTATCGC GGTTGATCTG CGCCTTTACT CGTGCCTGTC GTGCTTTCTG    3060

CTTGTGTTTT TGCTGTTGTT TGTCGCTCAT GTGGATTCAC CTCCATCGGT GTCCGATGTT    3120

CGTGCTAGCC GAATTTCGAG AACCTGATTT CTGAGAGTCA TATCGGTGAT CGCCACGTCC    3180

GGCCGGTCGA GTACGACTCG CTCGACCACG TCGTCGTCGA CGCGTAGCGT GAGTGCCTGC    3240

TCGTCGGTAT CGAGTGCGAC GTCGACGTCG TCGTCCGTCA CGCCCGGCAA ATCTGCGACC    3300

ACGACGAGTT CGTCGCCGCT CGTTCCTCCA CGAGTCTCGA CGTGAATCGA ATCCTCCGTC    3360

GTCCTTTGCT GACCGGATCG CTGTTCGGAG CGGGACCGAT TGGACGATGG TTCCTCGTCG    3420

TAGGACGACC CGTCCGCTCG TCCCAGCCCG ATGGAAACGT CGTAGTCGTA ATCAATTCGG    3480

GCGTTTCCCC GGTCGATACG GCCTGACTCG TGTCGGTGAC CGCCCTCCTC TTCGATGTCG    3540

GCGAGCACCT CGACGAGCGT GTGCAATTGG TCGAGCAGCC CGCTGAGCTG GGAAGACTGG    3600

TCGTCGGACG CGTCGTCGTT TTCGTCGGGT ACCATTATTT CTTGACCTCC ATGCGGTCAC    3660

GCATCTGTTC TTGGACCTGC TCGGCCATCT CCAGTTGCGA TTCGAGTGCT TGCTTGCGCT    3720

GCTGGTACTC CTCGTCGGAT CGTTCACCAA CTTCGTACAG GAGTTGGTTC TCCTTGATGT    3780

CGTCTCGAAT CGATTTGGTG TCGTACATCT CGTCGAGAGC CATCGTCTGG AGGATATCCA    3840

GCAAGGAGAA AAACGGGCTC ACGAAGAGAT CGTCTATGAT GAACATGCAT TATCGGCCTC    3900
```

-continued

| | | | | | |
|---|---|---|---|---|---|
| CTTGTTGCTG | TTCCGCGCCG | ATGTGAATGT | CCACGAAATT | GTACGGCGGC | CACGGCCCCG | 3960 |
| TGTACTGAAT | CGTCAGTTCG | TCGTATTCCG | CTTCGACATC | GTCGATGGCG | GAGTCGAAAG | 4020 |
| CATCGCGTTT | CTCGAAGTCG | ACGAGGTACG | ACTTATTGAT | GATCAGGCGG | TCTGTGAAGA | 4080 |
| GATCGTTCTC | GGTCTCGTTG | ATACTCAGAT | CTGCTAGTTG | ATCCGTGACG | TTTTCCTGGA | 4140 |
| TTTCTTCTCG | AGGGACTGTA | TCGTCGCCAG | GACCGAGTAT | CTTCACGCCA | AGTTCGACGG | 4200 |
| TTCCCTCGAT | GTCATTCAGC | GTACTGCGCA | ATGCACGTCG | CGCCCGCGC | AATACACCCT | 4260 |
| TTAGCGTGCG | CGCACTTTTG | AACGCCATCC | CGAAGCTCAT | CGGGACGACT | GTGCGTTCTT | 4320 |
| CTTCGTGCTT | CAATACCTCC | TGGAGCACGT | TGTTATGAGC | TTCCACGTCC | TCATCGGTGC | 4380 |
| GCTCGGGGTC | GGTCGTATCA | ATGTCAGAGA | CGACAGCGGA | GAGTGTCTTG | TAATCGACCG | 4440 |
| TATAGACCTG | TTCCGCTCCG | GCAACGCCTT | CGACATCTAA | TTCGAGATCT | TCCTGTTCGA | 4500 |
| TGATACCGTA | TGTGTATAGG | TTCTCAGTCA | TTGGTCTCTC | TTCCTTGGGA | TTGTGATTGA | 4560 |
| CGCGCCTTGC | AATCGGTCAT | AACCGCCTTG | AGTACGAGCG | AAAACAGCAG | CAACTGATCA | 4620 |
| ACCATGTGGT | CTATTCGGGT | GAACGCTCCT | TCAGGATCGG | AGAGGCGATA | CACTTTGCGC | 4680 |
| TTGCTCAATT | TCTGTACCTC | AAGTACACCT | TCGACTGCAA | GGTCATTTAA | ATGCGGGTAT | 4740 |
| ACTGTACCCG | GACTCAGGTC | TGCCCCAAAC | AGCCGCCGGA | GATCCTGGAG | CAGTTCTTTT | 4800 |
| CCACAGGCAC | CGTCTCGCAC | AGTAATCAGA | AGAAGGAGAA | TCTCGTCGAT | ATGTTCGGTG | 4860 |
| ACGATGGCAT | CACTGATCGT | GTGAAGCTGG | TCATTATCAA | GCCACCCGTC | CATCGTAGCG | 4920 |
| ACCGCGTCAT | CAGTCAGCGG | CGTGTCCGTG | TAGCGTTGCG | TTGCCCCCTC | ATCAGGCGGC | 4980 |
| TGGTCTGCGT | GATCTGACGC | ACCGTCGGAT | TCGATCACTG | ATTCGAGATC | TGTGACTGCG | 5040 |
| AACGAGATCG | CGGCGTTAGC | ATCGATGTCT | GCGGTGAGTT | CCTCCAGCAA | GTCGTCCATT | 5100 |
| GTTAGACCAT | CTCCGTGAGC | GTGATTTTGG | GGATCGACTC | TGACTGGCTG | ATGCCGATTC | 5160 |
| CGAGCAGGGG | CGTCAACGGG | TTTTCGCCAT | ACAGGATGAT | GGCGTCACCG | GACCGTTCCA | 5220 |
| GCCGGAAGTG | CATATCGGCA | ACCCGATCCG | CTCGCGTGCG | GAGTTCAGTA | CCTTGCTTGG | 5280 |
| TGATGAGCAG | TGTCAGGTCG | TTGTGGAGAG | CGACGTAATT | TGCAAAGTCA | CCTAGCCGGG | 5340 |
| TCTCAAATGC | CTCCTGCGCC | GTGTCCATGC | TGATCACGTG | CAACAACGGA | TCTTCACTTT | 5400 |
| CTTCTCGCAC | CTGTTCAACG | TAGGCCATGT | ATGGCTCGTA | CGCGAGTTGC | CCGCCCTCTA | 5460 |
| TCGGTGACTC | AAAGTCCTCA | TCAATCGGAT | GCGGCTGGTC | ACTCCCCGTA | ACTCCATCCG | 5520 |
| TCGAACGTGA | GCCATCGTCC | GCACCATCAG | TCTCATGCGT | CGCCGTCGGT | GCATCGTCCG | 5580 |
| GCGGCGTTGT | CGTTGCCATC | TCAGAAAATG | ACTCAGTGCT | GTCCGGTTGG | TCGTACCGAT | 5640 |
| CCGCACTGTC | AGAGGGGCCG | GCGTATGTTT | CGAAGACGTG | GCAGTAGGTA | TCGAAGACCT | 5700 |
| GTGAGGAGAG | CACAGTATTG | AGATCGTTGT | GGAGTAAGCC | AGGGCTGCCC | TCCCGGGGCG | 5760 |
| GGACAACCGC | AACCCCCATC | TCCTGAGAGA | GGAAGTTGCG | AATCGTCGGG | AGCGTCAACA | 5820 |
| CGCTCCACGC | GTCACGAGAC | AGATCGGGCC | CGAGGTCGAG | ATGAACGACG | CTGCCGCGGT | 5880 |
| TGTAGCCACC | CGAGAGGATA | CGGTCAAGAT | CACGGATGCC | AGTCGAGAAT | TCGCCTTCG | 5940 |
| AATTTGCCAG | GGGATCCCAC | GTGCCATTCC | CGGTTCCTGT | TTGGATGGTT | AGTAATTCGA | 6000 |
| CCGGCGTGAT | CACCTGGAAC | TGGCCGTCGG | CAAGCGTAAA | GGGCTGTAAG | CGGTTGCCGA | 6060 |
| TTCGAACGCC | CCGAAGCTTA | TCCAAGCGGA | GATCCCGACG | CGTTCGGCCA | CGGTCATCCT | 6120 |
| CCTTAACCTG | GAGGGTGACG | ACCCCATCGA | CGATGTATTC | AAGCGATGAG | GGCGCCGCTG | 6180 |
| TTTCTGTCAC | TAACATCAGA | CGAATGTTCT | CTTCGCGGGC | AAGAACGGCC | AGTTGATTCG | 6240 |
| TCACAGTCTT | GATGTCAGGG | GGGTCATCGT | GGCGAACAGC | CAAATACTCG | TAGATGAGTT | 6300 |

```
CCCAGCTATC GAATGCGATT GTGAGTTGCG TGGTCGCGGC GTTGATCTCT TGGATCCATT      6360

CGAGGAGCGA ATCCAGATCG AGTTTCTCGA ATGGCACGTC TACGTCCAGT GGGAGTTCGA      6420

ATGGGTCTTG GAAGAGGTCA AGAATCGCGG TTGTGTCGAG TGAGGAGTGA TCGGCGAAGT      6480

ACATCTCGTG AACCGTCTCC TGATCAACAC GTGTGGACAC GTAGAGGACA TCACTGTCTC      6540

GGTCCAACAC ATCGAGGCCG CGGATCGTGA ACAAGGTCTT ACCCGTGCCT GGTGCACCGT      6600

TAATGAGGAG CGTTTCCCCG GCGTCACCCA TGAAAAACTG GCTGAGCTCG CGGGGGAATA      6660

ACACGATTCC GGTGTAGTCT GTGGGCGGGT GAGCTAGATT GGGTGAACTC ATTACTTCTC      6720

TCCAGTCGAT GGCGGTAGAG CACTCCCGAC TAGTAGGTGA GGCTTTCTTC GCTTCACGAC      6780

TGTCTAAGAA GCTTTACACT CTCCGTACTT AGAAGTACGA CTCATTACAG GAGACATAAC      6840

GACTGGTGAA ACCATACACA TCCTTATGTG ATGCCCGAGT ATAGTTAGAG ATGGGTTAAT      6900

CCCAGATCAC CAATGGCGCA ACCAGATTCT TCAGGCTTGG CAGAAGTCCT TGATCGTGTA      6960

CTAGACAAAG GTGTCGTTGT GGACGTGTGG GCTCGTGTGT CGCTTGTCGG CATCGAAATC      7020

CTGACCGTCG AGGCGCGGGT CGTCGCCGCC TCGGTGGACA CCTTCCTCCA CTACGCAGAA      7080

GAAATCGCCA AGATCGAACA AGCCGAACTT ACCGCCGGCG CCGAGGCGGC ACCCGAGGCC      7140

TGACGCACAG GCCTCCCTTC GGCCGGCGTA AGGGAGGTGA ATCGCTTGCA AACCATACTA      7200

TTAACACCTT CTCGGGTACA CACTAATCCC ATGAGTGTCA CAGACAAACG CGACGAGATG      7260

AGTACTGCCC GCGATAAGTT CGCAGAATCA CAGCAGGAGT TCGAATCATA CGCTGACGAG      7320

TTTGCAGCCG ATATCACGGC AAAGCAAGAC GATGTCAGCG ACCTTGTCGA TGCGATCACC      7380

GACTTCCAGG CGGAGATGAC CAACACGACG GATGCATTTC ACACATATGG TGACGAGTTC      7440

GCCGCTGAGG TTGACCACCT CCGTGCCGAT ATTGACGCCC AGCGGGACGT GATCCGTGAG      7500

ATGCAGGATG CGTTCGAGGC ATATGCTGAC ATCTTCGCTA CAGATATCGC AGACAAACAA      7560

GATATCGGCA ATCTTCTGGC TGCGATTGAG GCGCTCCGAA CAGAGATGAA CTCAACCCAC      7620

GGGGCATTCG AAGCATATGC GGACGACTTC GCAGCCGATG TCGCTGCGCT CCGTGATATA      7680

TCTGATCTGG TTGCAGCAAT CGACGACTTC CAAGAGGAAT TCATCGCCGT GCAGGACGCA      7740

TTTGACAACT ACGCTGGTGA CTTCGATGCG GAGATCGACC AGCTCCACGC TGCCATCGCT      7800

GACCAGCACG ACAGCTTCGA CGCTACCGCG GACGCCTTCG CAGAGTACCG AGATGAGTTC      7860

TATCGCATAG AGGTGGAAGC ACTGCTTGAG GCGATCAACG ACTTCCAGCA GGACATCGGT      7920

GACTTCCGAG CGGAGTTTGA AACGACTGAG GACGCGTTCG TTGCCTTCGC CCGTGACTTC      7980

TATGGCCACG AGATCACGGC CGAGGAAGGC GCCGCCGAAG CGGAAGCCGA ACCCGTCGAG      8040

GCTGACGCGG ACGTCGAAGC GGAAGCAGAA GTCTCTCCAG ACGAAGCTGG CGGAGAATCC      8100

GCCGGTACCG AGGAAGAAGA GACAGAGCCG GCCGAGGTGG AAACAGCGGC TCCAGAAGTA      8160

GAGGGGAGTC CTGCGGACAC GGCAGACGAA GCGGAAGATA CGGAAGCAGA GGAGGAGACA      8220

GAGGAAGAGG CACCGGAAGA CATGGTGCAG TGCCGGGTGT GCGGCGAATA CTATCAGGCC      8280

ATCACGGAGC CCCATCTCCA GACCCATGAT ATGACGATTC AGGAGTACCG CGACGAGTAC      8340

GGTGAGGATG TCCCCCTTCG GCCGGATGAT AAAACATGAC GAACGAGTCC CGTAAACGCA      8400

AGGTACGAGG GTCGCAGATC CGCTCCTCAC GCGGCGACAA GAAACAGGGG CGATCACAGA      8460

GCCGTGATGA TAAGGAGATC GAGCGTCTCG AGAGGCAGAA CGACGCTCGT GGCCAGGAGT      8520

CGTCTACCCA CGTCGACGAG GGGTTCGTTC CCGAGGAACA GTCCTTCATC GAGACCGAAT      8580

CGGTCAATCG AGTCGAGTCG CGGATGGAAC GGTGGCTCGA TGTCGGACGT CCGGTTCACC      8640

TGATCGGGCC GACCGGCTGT GGGAAAACGT CGCTGGCGAT GCACGTCGCG CGCGAGCGCG      8700
```

-continued

| | | | | | |
|---|---|---|---|---|---|
|ATCGCCCGGT|CGTCTGGATC|AACGGCGACG|CCGAACTCAC|GACCAGCGAT|CTCGTCGGCG|8760|
|AATACGCGGA|AAAAGAGCGC|ATCTCGGAGC|ACGATCAATT|CATCCACAAC|GTCGTTAAGA|8820|
|GCAAGGACAT|CATCCGTGAT|CGATGGGTGG|ACAACCCCCT|GACGCTCGCC|GTACAAGAGG|8880|
|GGGCAACGCT|GGTCTACAAC|GAGTTCTCCC|GCACCAAGCC|CGTCGCAAAC|AACGTGCTGT|8940|
|TGTCGGTCTT|CGAGGAAGGG|GTGCTCGAAC|TGCCGGGGAA|ACGCGGCAAA|TCTCGGTATG|9000|
|TAGATGTGCA|TCCTGAGTTC|CGAACCATCC|TGACCTCGAA|CTCCGTCGAG|TACGCTGGCG|9060|
|TCCACGAGCC|GCAAGACGCC|CTGCTCGACC|GCCTCATCGG|GATCTACATG|GATTTCTACG|9120|
|ATCTCGACAC|GGAGATCGAG|ATCGTTCGGG|CGCACGTCGA|CAAGTCGGCC|GACACAAACG|9180|
|TCGAGGACAT|CGTGCGGGTT|CTGCGTGAAC|TCCGCGAGCG|GCTCGATATC|ACCGTGGGTA|9240|
|CACGGGCCGC|GATTATGGCC|AACGAAGGCG|CTACCACCGT|CGACACCGTC|GACCAGGCCG|9300|
|TCCTGACCGA|TATCTGTACC|GACGTGCTGG|CATCGAAGGT|CGCCCAGCGG|AGCGACGTTC|9360|
|GCGGGCTGCG|CGAAGAAATA|GAATCCGCGA|TCGACGACAT|GGAAGTCGCC|CTTTCTTAAG|9420|
|ATCCGGGGTC|TCTACATAGA|AGCATGGCAG|ATCCAGCAAA|CGATCGATCT|GAACGCGAGG|9480|
|AAGGCGGCGA|GGACGACGAA|ACACCGCCAG|CGTCCGACGG|GAACCCCTCG|CCGTCGGCCA|9540|
|ATTCATTCAC|TCTCTCCAAC|GCGCAGACGC|GCGCACGAGA|GGCGGCACAG|GACCTGTTGG|9600|
|AACACCAGTT|CGAGGGATTG|ATCAAAGCCG|AGTCGAACGA|CGAAGGCTGG|CGGACCGTCG|9660|
|TCGAAGTCGT|CGAACGGAAC|GCCGTACCCG|ATACACAAGA|CATCATCGGT|CGCTACGAGA|9720|
|TCACGCCTTG|ACGGGACGGG|GGACGTCACC|GGCTACGAGC|TCCTAGAACG|CTATCGTCGG|9780|
|GGCGACATGA|AAGAGGAACT|GTAGCGGTGC|GTCAAATGCA|CGAGCAATAG|ATATGGCCCA|9840|
|TCGACTGACC|GTAGCGAACG|AGAAAGGCGG|CGTGGGGAAG| | |9880|